(12) United States Patent
Lentz et al.

(10) Patent No.: US 11,819,233 B2
(45) Date of Patent: Nov. 21, 2023

(54) DEVICES AND TECHNIQUES FOR SEPARATING TISSUE

(71) Applicant: Medtronic Xomed, Inc., Jacksonville, FL (US)

(72) Inventors: Linnea R. Lentz, Stacy, MN (US); Michael A. Schugt, St. Paul, MN (US)

(73) Assignee: Medtronic Xomed, Inc., Jacksonville, FL (US)

( * ) Notice: Subject to any disclaimer, the term of this patent is extended or adjusted under 35 U.S.C. 154(b) by 44 days.

(21) Appl. No.: 16/752,049

(22) Filed: Jan. 24, 2020

(65) Prior Publication Data
US 2021/0228226 A1 Jul. 29, 2021

(51) Int. Cl.
| | | |
|---|---|---|
| *A61B 17/32* | (2006.01) | |
| *A61B 17/34* | (2006.01) | |
| *A61B 5/00* | (2006.01) | |
| *A61B 17/3211* | (2006.01) | |
| *A61N 1/05* | (2006.01) | |
| *A61N 1/08* | (2006.01) | |

(Continued)

(52) U.S. Cl.
CPC .... *A61B 17/32002* (2013.01); *A61B 17/3468* (2013.01); *A61B 5/4818* (2013.01); *A61B 2017/32113* (2013.01); *A61N 1/0548* (2013.01); *A61N 1/08* (2013.01); *A61N 1/3601* (2013.01); *A61N 1/37211* (2013.01)

(58) Field of Classification Search
CPC .......... A61B 17/32002; A61B 17/3468; A61B 17/3211; A61B 17/320016; A61B 17/32; A61B 5/4818; A61B 2017/32113; A61B 2017/320024; A61B 2017/320028; A61B 2017/320032; A61N 1/08; A61N 1/3601; A61N 1/37211; B26B 1/08; B26B 1/02; B26B 1/00; B26B 5/001
See application file for complete search history.

(56) References Cited

U.S. PATENT DOCUMENTS

| | | |
|---|---|---|
| 5,146,918 A | 9/1992 | Kallok et al. |
| 5,540,733 A | 7/1996 | Testerman et al. |
| 5,546,952 A | 8/1996 | Erickson |

(Continued)

FOREIGN PATENT DOCUMENTS

| | | |
|---|---|---|
| EP | 3071288 B1 | 11/2018 |
| WO | 2017087681 A1 | 5/2017 |

OTHER PUBLICATIONS

International Search Report and Written Opinion of International Application No. PCT/US2021/014074, dated Apr. 15, 2021, 13 pp.

(Continued)

*Primary Examiner* — Erich G Herbermann
(74) *Attorney, Agent, or Firm* — Shumaker & Sieffert, P.A.

(57) ABSTRACT

Devices, systems, and techniques are described for creating pockets in tissue for accepting implantable medical devices. For example, a surgical tool includes a shaft defining a proximal end, a distal end, and a longitudinal axis, a handle coupled to the proximal end of the shaft, and one or more blades configured to move between a retracted configuration and a deployed configuration, wherein the one or more blades extend, in the deployed configuration, substantially perpendicular to the longitudinal axis at the distal end of the shaft. The one or more blades may be configured to separate tissue in the deployed configuration.

18 Claims, 19 Drawing Sheets

(51) Int. Cl.
  *A61N 1/36* (2006.01)
  *A61N 1/372* (2006.01)

(56) References Cited

U.S. PATENT DOCUMENTS

| | | | |
|---|---|---|---|
| 5,549,655 | A | 8/1996 | Erikcson |
| 5,591,216 | A | 1/1997 | Testerman et al. |
| 6,044,297 | A | 3/2000 | Sheldon et al. |
| 6,269,269 | B1 | 7/2001 | Ottenhoff et al. |
| 6,345,202 | B2 | 2/2002 | Richmond et al. |
| 6,358,251 | B1* | 3/2002 | Mirza ............... A61B 17/1617 606/172 |
| 7,845,357 | B2 | 12/2010 | Buscemi et al. |
| 8,366,615 | B2 | 2/2013 | Razavi |
| 8,588,941 | B2 | 11/2013 | Mashiach |
| 8,744,589 | B2 | 6/2014 | Bolea et al. |
| 8,751,005 | B2 | 6/2014 | Meadows et al. |
| 8,813,753 | B2 | 8/2014 | Bhat et al. |
| 8,888,781 | B2* | 11/2014 | Sterrett ............. A61B 17/3472 606/80 |
| 8,909,341 | B2 | 12/2014 | Gelfand et al. |
| 9,486,628 | B2 | 11/2016 | Christopherson et al. |
| 9,643,004 | B2 | 5/2017 | Gerber |
| 9,662,045 | B2 | 5/2017 | Skelton et al. |
| 9,662,497 | B2 | 5/2017 | Meadows et al. |
| 9,757,560 | B2 | 9/2017 | Papay |
| 9,849,289 | B2 | 12/2017 | Mashiach et al. |
| 9,884,191 | B2 | 2/2018 | Meadows et al. |
| 9,888,864 | B2 | 2/2018 | Rondoni et al. |
| 9,889,299 | B2 | 2/2018 | Ni et al. |
| 9,895,541 | B2 | 2/2018 | Meadows et al. |
| 10,029,098 | B2 | 7/2018 | Papay |
| 10,065,038 | B2 | 9/2018 | Papay |
| 10,195,428 | B2 | 2/2019 | Scheiner |
| 10,744,339 | B2 | 8/2020 | Makansi |
| 2002/0049479 | A1 | 4/2002 | Pitts |
| 2003/0191474 | A1 | 10/2003 | Cragg et al. |
| 2003/0199874 | A1* | 10/2003 | Michelson ......... A61B 17/1757 606/86 A |
| 2003/0216789 | A1 | 11/2003 | Deem et al. |
| 2006/0184188 | A1 | 8/2006 | Li et al. |
| 2007/0123950 | A1 | 5/2007 | Udlow et al. |
| 2007/0173893 | A1 | 7/2007 | Pitts |
| 2008/0103407 | A1 | 5/2008 | Bolea et al. |
| 2008/0161874 | A1 | 7/2008 | Bennett et al. |
| 2008/0195128 | A1 | 8/2008 | Orbay |
| 2008/0208230 | A1 | 8/2008 | Chin et al. |
| 2009/0270962 | A1 | 10/2009 | Yang et al. |
| 2011/0270339 | A1 | 11/2011 | Murray, III et al. |
| 2011/0270340 | A1 | 11/2011 | Pellegrini et al. |
| 2013/0253309 | A1 | 9/2013 | Allan et al. |
| 2013/0253342 | A1 | 9/2013 | Griswold et al. |
| 2013/0253343 | A1 | 9/2013 | Waldhauser et al. |
| 2013/0253344 | A1 | 9/2013 | Griswold et al. |
| 2013/0253345 | A1 | 9/2013 | Griswold et al. |
| 2013/0253346 | A1 | 9/2013 | Griswold et al. |
| 2013/0253347 | A1 | 9/2013 | Griswold et al. |
| 2014/0031891 | A1 | 1/2014 | Mashiach |
| 2014/0135868 | A1 | 5/2014 | Bashyam |
| 2014/0228905 | A1 | 8/2014 | Bolea |
| 2014/0323839 | A1 | 10/2014 | MCCreery |
| 2015/0100106 | A1 | 4/2015 | Shishilla et al. |
| 2017/0151432 | A1 | 6/2017 | Christopherson et al. |
| 2018/0117316 | A1 | 5/2018 | Wagner et al. |
| 2019/0059910 | A1* | 2/2019 | Adams ............... A61B 17/1624 |
| 2020/0269044 | A1 | 8/2020 | Papay |
| 2020/0338358 | A1 | 10/2020 | Makansi |
| 2020/0346017 | A1 | 11/2020 | Caparso et al. |

OTHER PUBLICATIONS

Gharb et al., "Microsurgical Anatomy of the Terminal Hypoglossal Nerve Relevant for Neurostimulation in Obstructive Sleep Apnea," Neuromodulation: Technology at the Neural Interface, Aug. 5, 2015, 8 pp.

Mu et al., "Human Tongue Neuroanatomy: Nerve Supply and Motor Endplates," Oct. 2010, accessed from NIH Public Access, 27 pp.

Heiser et al., "Surgical anatomy of the hypoglossal nerve: a new classification system for selective upper airway stimulation," Wiley Online, May 22, 2017, 10 pp.

Medtronic, "Basic Evaluation Procedure Technique Without Fluoroscopy—Part 3: Needle Placement," Training Video accessed from https://www.medtronic.com/us-en/healthcare-professionals/therapies-procedures/urology/sacral-neuromodulation/education-training/videos.html, webpage last updated Feb. 2018, 8 pp.

Medtronic, "Basic Evaluation Procedure Technique Without Fluoroscopy—Part 4: Test Lead Placement," Training Video accessed from https://www.medtronic.com/us-en/healthcare-professionals/therapies-procedures/urology/sacral-neuromodulation/education-training/videos.html, webpage last updated Feb. 2018, 8 pp.

Medtronic, "Basic Evaluation Procedure Technique Without Fluoroscopy—Part 5: Securing & Connecting Test Leads," Training Video accessed from https://www.medtronic.com/us-en/healthcare-professionals/therapies-procedures/urology/sacral-neuromodulation/education-training/videos.html, webpage last updated Feb. 2018, 8 pp.

U.S. Appl. No. 62/814,398, naming inventor Avram Scheiner, filed Mar. 6, 2019.

International Preliminary Report on Patentability from International Application No. PCT/US2021/014074 dated Aug. 4, 2022, 8 pp.

\* cited by examiner

DEVICES AND TECHNIQUES FOR SEPARATING TISSUE

TECHNICAL FIELD

This disclosure relates to surgical procedures and, more particularly, to devices and techniques for separating tissue.

BACKGROUND

Medical devices may be implanted and may be used to monitor one or more physiological conditions and/or deliver therapy, such as electrical stimulation therapy to patients via various tissue sites to treat a variety of symptoms or conditions. Example symptoms or conditions may include obstructive sleep apnea (OSA), chronic pain, tremor, Parkinson's disease, epilepsy, urinary or fecal incontinence, sexual dysfunction, obesity, or gastroparesis. In one example, medical device may deliver electrical stimulation therapy via one or more leads that include electrodes located proximate to target locations associated with the tongue for OSA, brain, the spinal cord, pelvic nerves, peripheral nerves, or the gastrointestinal tract of a patient. These and other medical devices are typically implanted beneath the skin, i.e., subdermally, at a location appropriate for monitoring and/or treating target tissue.

SUMMARY

The devices, systems, and techniques of this disclosure generally relate to separation of tissue for creating a pocket configured to accept an implantable medical device. However, such tissue separation tools and techniques may be used for other surgical purposes in other examples, such as removal of tissue, trauma repair, etc. As described herein, a surgical tool may include one or more blades that are extendable from a retracted configuration to a deployed configuration. When in the retracted configuration, a clinician may insert the blades through the skin and into the desired tissue. When the blades are at the appropriate depth, the clinician may actuate a control to extend the blades into the deployed configuration. For example, the blades may extend approximately perpendicular to the shaft of the surgical tool in the deployed configuration. Once in the deployed configuration, the clinician may rotate the one or more blades, either by rotating the entire tool or by rotating the blades via a rotatable internal mechanism within the shaft, to cause the one or more blades to cut through and separate tissue superficial to the blades from tissue deep of the blades. Once the tool is removed, the clinician may implant a medical device within the pocket formed by the separation of tissue.

In one example, a surgical tool includes a surgical tool that includes a shaft defining a proximal end, a distal end, and a longitudinal axis, a handle coupled to the proximal end of the shaft, and one or more blades configured to move between a retracted configuration and a deployed configuration, wherein the one or more blades extend, in the deployed configuration, substantially perpendicular to the longitudinal axis at the distal end of the shaft, and wherein the one or more blades are configured to separate tissue in the deployed configuration.

In another example, a method includes inserting a distal portion of shaft of a surgical tool into tissue of a patient, the shaft defining a distal end, a proximal end, and a longitudinal axis, moving one or more blades from a retracted configuration to a deployed configuration, wherein the one or more blades extend, in the deployed configuration, substantially perpendicular to the longitudinal axis at the distal end of the shaft, and rotating the one or more blades in the deployed position to separate a first portion of tissue from a second portion of tissue such that an implantable medical device is insertable between the first portion of tissue and the second portion of tissue.

In another example, a surgical tool includes a surgical tool that includes a shaft defining a proximal end, a distal end, and a longitudinal axis, a handle coupled to the proximal end of the shaft, one or more blades configured to move between a retracted configuration and a deployed configuration, wherein the one or more blades extend, in the deployed configuration, substantially perpendicular to the longitudinal axis at the distal end of the shaft, the one or more blades are attached to the distal end of the shaft via a hinge, and wherein the hinge is configured move the blades between the retracted configuration and the deployed configuration, and each blade of the one or more blades comprises a length between approximately 1.0 cm and 8.0 cm, the length being greater than a width of the one or more blades, a depth stop disposed at an axial position along the shaft, wherein the depth stop is configured to contact skin and prevent the shaft and the one or more blades from being inserted further into tissue, and a control mechanically coupled to the one or more blades, wherein actuation of the control pivots the hinge between the retracted configuration and the deployed configuration.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
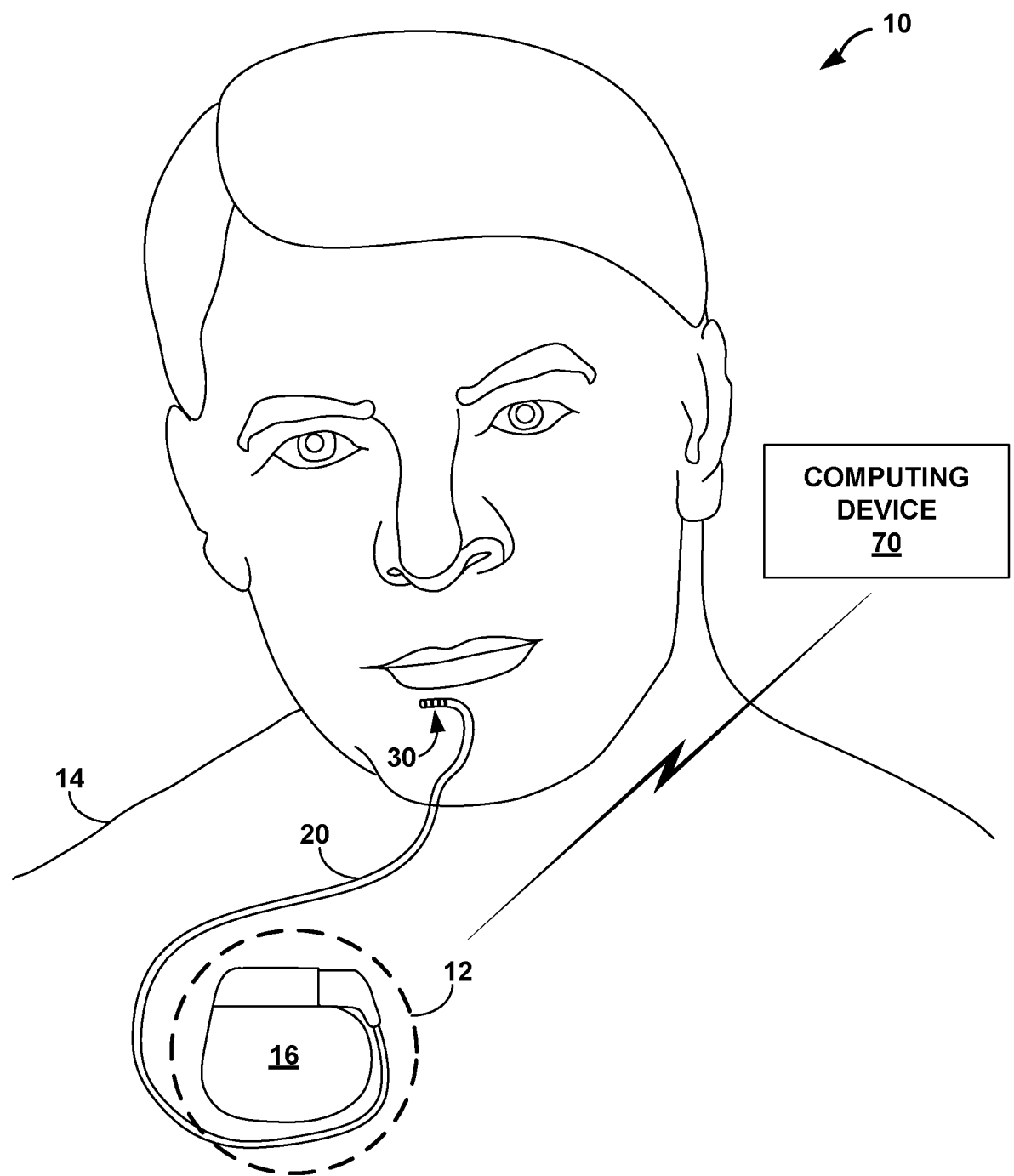
FIGS. 1 and 2 are conceptual diagrams of an implantable medical device (IMD) system for delivering obstructive sleep apnea (OSA) therapy.

The devices, systems, and techniques of this disclosure generally relate to separation of tissue for creating a pocket configured to accept an implantable medical device. Implantable medical devices (IMDs) are typically implanted deep, or beneath, the skin or dermis. In some examples, one or more leads or catheters may be tunneled to the IMD and coupled to the IMD. Before the IMD can be implanted, a space within tissue (e.g., a pocket or tissue pocket) may need to be created in order for the IMD to fit within the tissue. A clinician may first create an incision in the skin near the desired location for the pocket. Then, the clinician may insert one or more fingers through the skin and into the underlying tissue which is typically adipose (i.e., fat) tissue. Using the fingers, the clinician may manually separate the tissue in the desired area until there is pocket having sufficient space to accept the IMD.

Although this manual pocket creation may be effective in some situations, there may be some drawbacks. For example, pocket creating using clinician fingers may result in more tissue separation than required, and longer healing times, or not enough tissue separation, and longer surgical time required for the clinician to reform an appropriately sized pocket. In addition, the manual pocket creation procedure may vary the depth of the pocket beneath the skin. This variation in depth may reduce recharging efficiency for the IMD. Some IMDs include rechargeable power supplies, where recharging power is received transcutaneously via inductive coupling or some other power transfer method. However, these wireless power transfer methods may be most efficient at certain distances between the recharge coil of the IMD and the recharge coil of the external charger. If the clinician creates a pocket that is too deep in tissue, or to shallow to the skin, the IMD may recharge less efficiently. Similar to wireless power transfer, an IMD implanted too deep in tissue may reduce wireless telecommunication signal strength between the IMD and an external device.

As described herein, a surgical tool is configured to cut through and separate tissue at a specified depth from the surface of the skin to create a tissue pocket, or tissue void, within which an IMD can be implanted. In this manner, the IMD implanted within the tissue pocket will be covered by the specified depth, or thickness, or skin. This surgical tool may reduce clinician time required to create the tissue pocket and reduce tissue trauma that may accompany more blunt tissue separate techniques. In addition, the surgical tool creating the tissue pocket at the specified depth may ensure that the thickness of tissue covering the IMD promotes a desired distance between the IMD and an external charger for efficient transfer of power to the IMD during wireless recharging of the IMD power source.

In some examples, the surgical tool may include one or more blades and a shaft, where the distal end of the shaft and the one or more blades are configured to be inserted into tissue of the patient. During insertion into the tissue, the one or more blades may be placed in a retracted configuration that enables the shaft to be inserted into the tissue. In some examples, the surgical tool may include graduated markings along the surface of the shaft to indicate the depth of the shaft below the external surface of the skin. In addition, or alternatively, the surgical tool may include a depth stop attached to an axial location of the shaft that prevents the shaft from further insertion into the tissue when the depth stop contacts the external surface of the skin. The specified depth for the tissue pocket (e.g., the thickness of tissue superficial from the IMD to be implanted within the patient), may be determined by the clinician based on patient anatomy, patient comfort, IMD size, lead location, etc. In some examples, the specified depth may be indicated by the manufacturer of the IMD according to the appropriate distance between the IMD and external charger for wireless recharging of the IMD power source. For example, the depth may be specified to be less than about 1 cm, less than about 2 cm, or less than about 3 cm. As another example, the specified depth may be set to enable effective wireless communication between the IMD and an external device.

Once the surgical tool is placed at the desired depth within the tissue (e.g., where the one or more blades can be deployed at a specified or desired depth from the exterior surface of the skin), the clinician may actuate the surgical tool to move the one or more blades into the deployed configuration from the retracted configuration. For example, the one or more blades may be configured to extend from a distal end of the shaft of the surgical tool in the deployed configuration. In the deployed configuration, the one or more blades may extend substantially perpendicular from a longitudinal axis defined by the shaft. Once the one or more blades are in the deployed confirmation, the clinician may rotate the one or more blades around the longitudinal axis of the shaft and within the tissue such that the blades slice through and separate the tissue in a plane. The clinician may continue the rotation until the one or more blades create a disk-shaped cut (e.g., a tissue pocket) in the tissue. Once the cut is complete, the clinician may move the one or more blades back into the retracted configuration and remove the surgical tool from the patient's tissue. The clinician may then insert an IMD within the tissue pocket within the separated tissue.

The surgical tools and techniques described herein may be used to create tissue pockets for the implantation of any types of IMDs at any appropriate tissue site of the patient. For example, the surgical tools may be used to create tissue pockets in the patient's chest, abdomen, lower back, upper buttocks, neck, or any other location. Therefore, IMDs can be implanted to provide therapies such as deep brain stimulation (DBS), spinal cord stimulation (SCS), peripheral nerve stimulation (PNS), pelvic floor stimulation, or any other types of therapy. As another example, the surgical tools described herein may be used to create a tissue pocket for an IMD configured to treat obstructive sleep apnea (OSA).

OSA encompasses apnea and hypopnea, is a disorder in which breathing may be irregularly and repeatedly stopped and started during sleep, resulting in disrupted sleep and reduced blood oxygen levels. Muscles in a patient's throat intermittently relax thereby allowing soft tissues of the throat to obstruct the upper airway while sleeping and cause OSA. In patients with a smaller than normal airway, airflow into the upper airway can be obstructed by the tongue or soft pallet moving to the back of the throat and covering the airway. Loss of air flow also causes unusual inter-thoracic pressure as a person tries to breathe with a blocked airway.

Lack of adequate levels of oxygen during sleep can contribute to abnormal heart rhythms, heart attack, heart failure, high blood pressure, stroke, memory problems, and increased accidents during the day due to inadequate sleep. Additionally, loss of sleep occurs when a person is awakened during an apneic episode.

Medical devices, systems, and techniques for implanting devices and/or delivering electrical stimulation to the protrusor muscles of the tongue for the treatment of obstructive sleep apnea (OSA) are described herein. Electrical stimulation is delivered to cause the tongue of a patient to enter a protruded state, during sleep, to avoid or reduce upper airway obstruction. As used herein, the term, "protruded state" with regard to the tongue refers to a position that is moved forward and/or downward compared to the non-stimulated position or a relaxed position of the tongue. The protruded state is a state associated with the contraction (e.g., via innervation from nerves and/or electrical stimulation) of protrusor muscles of the tongue (also sometimes referred to as "protruder" muscles of the tongue) including the genioglossus and geniohyoid muscles. A protruded state may be the opposite of a retracted and/or elevated position associated with the contraction of the retractor muscles (e.g., styloglossus and hyoglossus muscles) which retract and elevate the tongue. Electrical stimulation is delivered to cause the tongue to move (e.g., by depolarizing the nerve(s) that innervate the genioglossus and/or geniohyoid muscles) to and maintain a protruded state. As discussed above, the protruded state may prevent collapse, open, or widen the upper airway of a patient to at least partially increase airflow (e.g., promote unrestricted or at least reduced restriction of airflow during breathing).

A surgeon implants one or more leads that each include one or electrodes into the tongue such that the electrodes are proximate to a hypoglossal nerve and/or motor points (e.g., one or more locations where axons of the hypoglossal nerve terminate at respective muscle fibers of the protrusor muscles). For example, there are two hypoglossal nerves in the tongue of the patient. In one example, one lead may be used to stimulate (e.g., by delivering electrical stimulation through electrodes of the lead) one of the two hypoglossal nerves, one lead may be used to stimulate both hypoglossal nerves, or two leads may be used, where each lead stimulates a respective one of the hypoglossal nerves. Stimulation of either or both hypoglossal nerves of the tongue can cause contraction of the protrusor muscles to reduce the effect of or prevent OSA. The surgical tools and techniques described herein may be used to implant an IMD configured to treat OSA.

There are multiple sets of motor points for each of the protrusor muscles on the left side and the right side. Each motor point may innervate one or more muscle fibers of the protrusor muscle. In one example, one lead may be used to stimulate motor points for the protrusor muscles on one side of the tongue, one lead may be used to stimulate motor points for protrusor muscles on both sides of the tongue, or two leads may be used, where each lead stimulates a respective set of motor points for the protrusor muscles on each side. Stimulation of either or both sets of motor points of the tongue can cause contraction of the protrusor muscles to reduce the effect of, or prevent, OSA.

This disclosure describes examples of techniques related to implantation of an IMD and/or one or more leads in the tongue for treatment of OSA. Although the example techniques are described with respect to OSA, the example techniques should not be construed as limited to OSA. Rather, the example techniques described in this disclosure may be applicable to IMD and/or lead implantation for treatment of various conditions including lead implantation for treatment of conditions where the lead is implanted in a location other than the tongue, as discussed herein.

FIG. 1 is a conceptual diagram of an example medical system 10 for delivering OSA therapy. In system 10, implantable medical device (IMD) 16 and lead 20 are implanted in patient 14. IMD 16 is implanted within a tissue pocket 12 beneath the skin of patient 14, such as superficial from an underlying pectoral muscle. Lead 20 is electrically and mechanically coupled to IMD 16 and tunneled from tissue pocket 12, through tissue of the chest and neck, and to the target stimulation site for electrodes 30. As shown in further detail in FIG. 2, electrodes 30 at the distal end of lead 20 may be disposed within one or more muscles of the tongue. Computing device 70 may be configured as a programmer or other device that communicates with IMD 16. Computing device 70 may, in some examples, be configured to wirelessly transmit power to IMD 16 for recharging the power source of IMD 16. In other examples, another device separate from computer device 70 may be configured to be an external charger for transmitting power for recharging the power source of IMD 16.

Figure 2:
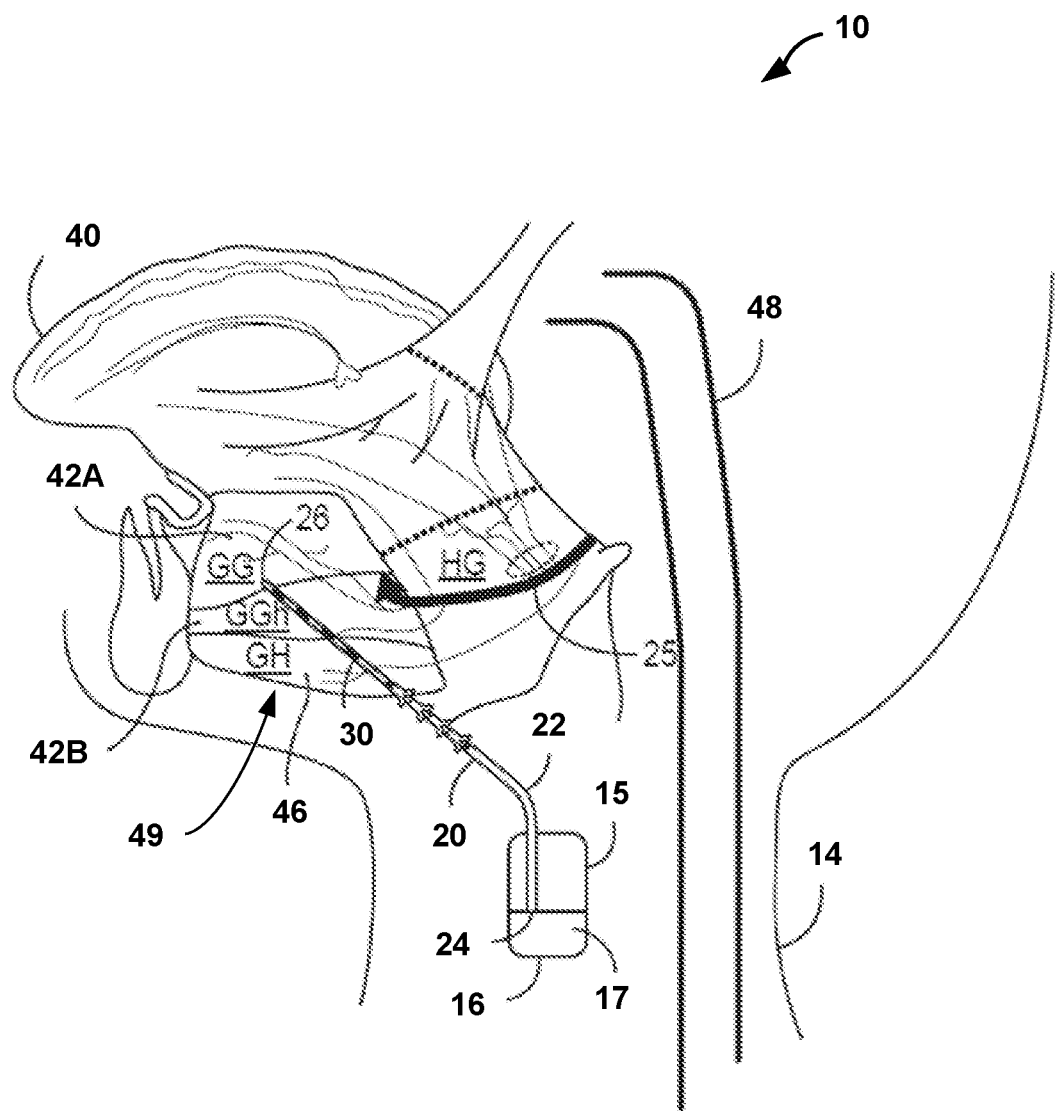

FIG. 2 is a conceptual diagram of medical system 10 for delivering OSA therapy. The illustration of FIG. 2 may be a side profile for patient 14 in contrast with the front view of patient 14 illustrated in FIG. 1. IMD 16 includes housing 15 enclosing circuitry of IMD 16. In some examples, IMD 16 includes connector assembly 17, which is hermetically sealed to housing 15 and includes one or more connector bores for receiving at least one medical electrical lead 20 used for delivering OSA therapy. Although one lead 20 is illustrated in FIG. 1, there may be one or more leads 20 to which IMD 16 is coupled. Housing 15 of IMD 16 may be in contact with the surrounding tissue of the tissue pocket when implanted within patient 14.

Lead 20 may include a flexible, elongate lead body 22 that extends from lead proximal end 24 to lead distal end 26. As illustrated, lead 20 includes one or more electrodes 30 that are carried along a lead distal portion adjacent lead distal end 26 and are configured for insertion within the protrusor muscles 42A, 42B, and 46 of tongue 40. As one example, the genioglossus muscle includes oblique compartment 42A and horizontal compartment 42B. In this disclosure, the genioglossus muscle is referred to as protrusor muscle 42. Protrusor muscle 46 is an example of the geniohyoid muscle.

While protrusor muscles 42 and 46 are described, the example techniques described in this disclosure are not limited to stimulating protrusor muscles 42 and 46. Also, FIG. 2 illustrates one set of protrusor muscles 42 and 46 (e.g., on a first side of tongue 40). The other side of tongue 40 also includes protrusor muscles. For instance, a left side of tongue 40 includes a first set of protrusor muscles 42 and 46, and a right side of tongue 30 includes a second set of protrusor muscles.

In some examples, a surgeon may implant one or more leads 20 such that one or more electrodes 30 are implanted within soft tissue, such as musculature, proximate to medial branches of one or both hypoglossal nerves. Leads 20 may be implanted such that one or more electrodes 30 may be generally in the area of the motor points (e.g., such that the motor points are within 1 to 10 mm from one or more electrodes 30). Examples of motor points for protrusor muscles 42 and 46 are illustrated in more detail with respect to FIG. 3B. Tongue 40 includes a distal end (e.g., tip of tongue 40), and electrodes 30 may be implanted proximate to the distal end of tongue 40. The surgeon may implant one or more leads 20 such that one or more electrodes are implanted proximate to bottom surface 49 of tongue 40, as illustrated in FIG. 2. In other examples, each lead 20 may be coupled to respective different IMDs (such as two different IMDs 16) implanted in distinct tissue pockets.

One or more electrodes 30 of lead 20 may be ring electrodes, segmented electrodes, partial ring electrodes or any suitable electrode configuration. Segmented and partial ring electrodes each extend along an arc less than 360 degrees (e.g., 90-120 degrees) around the outer perimeter of lead 20. In this manner, multiple segmented electrodes may be disposed around the perimeter of lead 20 at the same axial position of the lead. In some examples, segmented electrodes may be useful for targeting different fibers of the same or different nerves at respective circumferential positions with respect to the lead to generate different physiological effects (e.g., therapeutic effects). In some examples, lead 20 may be, at least in part, paddle shaped (e.g., a "paddle" lead), and may include an array of electrodes on a common surface, which may or may not be substantially flat.

As described above, in some examples, electrodes 30 are within musculature of tongue 40. Accordingly, one or more electrodes 30 may be "intramuscular electrodes." Intramuscular electrodes may be different than other electrodes that are placed on or along a nerve trunk or branch, such as a cuff electrode, used to directly stimulate the nerve trunk or branch. The example techniques described in this disclosure are not limited to intramuscular electrodes and may be extendable to electrodes placed closer to a nerve trunk or branch of the hypoglossal nerve(s). Also, in some examples, rather than one or more electrodes 30 being "intramuscular electrodes," one or more electrodes 30 may be implanted in connective tissue or other soft tissue proximate to the hypoglossal nerve. In some examples, rather than stimulating hypoglossal nerves, the examples described in this disclosure may be configured for stimulating the motor points, as described in more detail with respect to FIG. 3B. Stimulating the motor points may result in indirect activation of the hypoglossal nerve, but may generally be stimulating at a different location than direct stimulation to the hypoglossal nerve. As a result, in some examples, simulation of one or more motor points may result in more precise activation of muscle fibers than may be possible with stimulation of the hypoglossal nerve itself.

In some examples, lead 20 may be configured for advancement through the soft tissue, which may include the protrusor muscle tissue, to anchor electrodes 30 in proximity of the hypoglossal nerve(s) that innervate protrusor muscles 42 and/or 46 and/or motor points that connect axons of hypoglossal nerve(s) to respective muscle fibers of protrusor muscles 42 and/or 46. However, in some examples, lead 20 may be configured for advancement through vasculature of tongue 40. As one example, a surgeon may implant lead 20 in the lingual veins near the hypoglossal nerve though venous access in the subclavian vein. In such examples, one or more electrodes 30 may be "intravascular electrodes."

As described above, electrical stimulation therapy generated by IMD 16 and delivered via one or more electrodes 30 may activate protrusor muscles 42 and 46 to move tongue 40 forward, to promote a reduction in obstruction or narrowing of the upper airway 48 during sleep. As used herein, the term "activated" with regard to the electrical stimulation of protrusor muscles 42 and 46 refers to electrical stimulation that causes depolarization or an action potential of the cells of the nerve (e.g., hypoglossal nerve(s)) or stimulation at the neuro-muscular junction between the nerve and the protrusor muscles (e.g., at the motor points) innervating protrusor muscles 42 and 46 and motor points and subsequent depolarization and mechanical contraction of the protrusor muscle cells of protrusor muscles 42 and 46. In some examples, protrusor muscles 42 and 46 may be activated directly by the electrical stimulation therapy.

Protrusor muscles 42 and/or 46, on a first side of tongue 40 (e.g., left or right side of tongue 40), may be activated by a medial branch of a first hypoglossal nerve, and the protrusor muscles, on a second side of tongue 40 (e.g., other of left or right side of tongue 40), may be activated by a medial branch of a second hypoglossal nerve. The medial branch of a hypoglossal nerve may also be referred to as the XIIth cranial nerve. The hyoglossus and styloglossus muscles (not shown in FIG. 1), which cause retraction and elevation of tongue 40, are activated by a lateral branch of the hypoglossal nerve.

One or more electrodes 30 may be used to deliver bilateral or unilateral stimulation to protrusor muscles 42 and 46 via the medial branch of the hypoglossal nerve or branches of the hypoglossal nerve (e.g. such as at the motor point where a terminal branch of the hypoglossal nerve interfaces with respective muscle fibers of protrusor muscles 42 and/or 46). For example, one or more electrodes 30 may be coupled to output circuitry of IMD 16 to enable delivery of electrical stimulation pulses in a manner that selectively activates the right and left protrusor muscles in a cyclical or alternating pattern to avoid muscle fatigue while maintaining upper airway patency. Additionally, or alternatively, IMD 16 may deliver electrical stimulation to selectively activate protrusor muscles 42 and/or 46 or portions of protrusor muscles 42 and/or 46 during unilateral stimulation of the left or right protrusor muscles.

For instance, in some examples, one lead 20 may be implanted such that one or more of electrodes 30 deliver electrical stimulation to stimulate the left hypoglossal nerve or motor points of protrusor muscles on the left side of tongue, and therefore cause the left protrusor muscles to activate. In such examples, the electrical stimulation from one or more electrodes 30 may not be of sufficient amplitude to stimulate the right hypoglossal nerve or motor points of protrusor muscles on the right side of tongue and cause the right protrusor muscles to activate. In some examples, one lead 20 may be implanted such that one or more of electrodes 30 deliver electrical stimulation to stimulate the right hypoglossal nerve or motor points of protrusor muscles on the right side of tongue, and therefore cause the right protrusor muscles to activate. In such examples, the electrical stimulation from one or more electrodes 30 may not be of sufficient amplitude to stimulate the left hypoglossal nerve or motor points of protrusor muscles on the left side of tongue and cause the left protrusor muscles to activate.

In some examples, one lead 20 may be implanted substantially in the middle (e.g., center) of tongue 40. In such examples, one or more electrodes 30 may deliver electrical stimulation to both hypoglossal nerves or motor points of both muscles on the both sides of tongue 40, causing both hypoglossal nerves or motor points to activate respective left and right protrusor muscles. It may be possible to utilize current steering and field shaping techniques such that one or more electrodes 30 deliver a first electrical stimulation that stimulates the left hypoglossal nerve or motor points of protrusor muscles on the left side of tongue 40 with little to no stimulation of the right hypoglossal nerve or motor points of protrusor muscles on the right side of tongue 40, and then one or more electrodes 30 deliver a second electrical stimulation that stimulates the right hypoglossal nerve or motor points of protrusor muscles on the right side of tongue with little to no stimulation of the left hypoglossal nerve. In this way, IMD 16 may stimulate one hypoglossal nerve or motor points and then the other hypoglossal nerve or other motor points, which can reduce muscle fatigue.

For instance, continuous stimulation may cause protrusor muscles to be continuously in a protruded state. This continuous contraction may cause protrusor muscles 42 and/or 46 to fatigue. In such cases, due to fatigue, the stimulation may not cause protrusor muscles 42 and/or 46 to maintain a protruded state (or higher intensity of the electrical stimulation may be needed to cause protrusor muscles 42 and/or 46 in the protruded state). By stimulating one set of protrusor muscles (e.g., left or right), a second set (e.g., other of left or right) of protrusor muscles can be at rest. Stimulation may then alternate to stimulate the protrusor muscles that were at rest and thereby maintain protrusion of tongue 40, while permitting the protrusor muscles 42 and/or 46 that were previously activated to rest. Hence, by cycling between alternate stimulation of the left and right protrusor muscles, tongue 40 can remain in the protruded state, while one of the first or second set of protrusor muscles is at rest.

In some examples, one lead 20 may be implanted laterally or diagonally across tongue 40 such that some of electrodes 30 on lead 20 can be used to stimulate the left hypoglossal nerve and/or motor points of the protrusor muscles on the left side of tongue 40 and some of electrodes 30 on the same lead 20 can be used to stimulate the right hypoglossal nerve and/or motor points of the protrusor muscles on the right side of tongue 40. In such examples, IMD 16 may selectively deliver electrical stimulation to a first hypoglossal nerve and/or first motor points of the protrusor muscles on the a first side of tongue 40 via a first set of one or more electrodes 30, and then deliver electrical stimulation to a second hypoglossal nerve and/or second set of motor points of the protrusor muscles on a second side of tongue 40 via a second set of one or more electrodes 30. This may be another way in which to reduce muscle fatigue.

Lead proximal end 24 includes a connector (not shown in FIG. 2) that may be coupled to connector assembly 17 of IMD 16 to provide electrical connection between circuitry enclosed by the housing 15 of IMD 16. Lead body 22 encloses electrical conductors extending from each of one or more electrodes 30 to the proximal connector at proximal end 24 to provide electrical connection between output circuitry of IMD 16 and the electrodes 30.

There may be various ways in which lead 20 is implanted in patient 14. As one example, a surgeon may insert a needle (also called introducer needle) through below the jaw and in tongue 40 starting from the back of tongue 40. The surgeon may insert the needle until the needle reaches proximate to the tip of tongue 40, angling the needle to be proximate to the hypoglossal nerve (e.g., left or right hypoglossal nerve) and to the motor points. In some examples, the needle may include one or more electrodes at the distal end, and the surgeon may cause the one or more electrodes of the needle to output an electrical stimulation, which in turn causes a physiological response such as activation of protrusor muscles 42 and/or 46 and protrusion of tongue 40. The surgeon may adjust the location of the needle based on the physiological response to determine a location in tongue 40 that provides effective treatment. Using a needle with stimulating electrodes is not necessary in every example.

Once the needle is in place, the surgeon may insert a guidewire (or simply "guide") through the needle and anchor the guidewire to tissue of tongue 40. Then, the surgeon may remove the needle.

The surgeon may place an introducer, which may or may not include a dilator, over the guidewire through the opening created by the needle. The introducer may be referred to as an introducer, introducer sheath, or introducer/dilator. In some examples, the introducer may optionally include one or more electrodes that the surgeon can use to stimulate tongue 40 to ensure that lead 20 will be located in the correct location, relative to the target nerve tissue (e.g., motor points). Once the introducer is in place, the surgeon may remove the guidewire. In some examples, the introducer may be flexible or curved to ease placement of the introducer in patient 14.

The surgeon may prepare lead 20 for insertion. In some examples, there may be an additional sheath placed over lead 20 that holds fixation member(s), such as those described with respect to FIG. 3A, in place. Use of such an additional sheath is not necessary in all examples. Because lead 20 may be highly flexible, in some examples, the surgeon may place a stylet through lead 20 to provide some rigidity and allow lead 20 to traverse through tongue 40. Use of a stylet may not be necessary in all examples.

The surgeon may put lead 20 through the introducer such that one or more electrodes 30 are proximate to the hypoglossal nerve (e.g., such that distal end 26 is near tip of tongue as one non-limiting example). Electrodes 30 may be proximate to the hypoglossal nerve and/or motor points of the protrusor muscles due to the needle creating an opening near the hypoglossal nerve and/or motor points of the protrusor muscle. The surgeon may then tunnel proximal end 24 of lead 20 back to a connection with IMD 16.

In this manner, the surgeon may implant one lead 20. In examples where two or more leads are implanted, the surgeon may perform steps similar to those described above.

The above describes some example techniques for lead placement, and the examples described in this disclosure should not be considered limited to such examples of lead placement. Moreover, in some examples, the surgeon may use imaging techniques, such as fluoroscopy, during implantation to verify proper placement of lead 20, the needle, and/or the introducer.

FIG. 2 illustrates the location of IMD 16 as being within or proximate to then neck of patient 14 for ease of illustration. However, IMD 16 may be implanted in various other locations, such as in the chest of patient 14 and within tissue pocket 12 illustrated in FIG. 1. In this manner, the surgeon may implant IMD 16 in the left or right pectoral region. For instance, the surgeon may plan on implanting IMD 16 in the left pectoral region unless another medical device is already implanted in the left pectoral region. The surgeon may then implant IMD 16 in the right pectoral region. There may other locations where the surgeon may implant IMD 16 such as the back of patient 14. The example techniques are not limited to any particular implant location of IMD 16. In any implant location, the surgical tools and techniques described herein may be used to create the tissue pocket within which IMD 16 may be implanted.

In accordance with one or more examples described in this disclosure, a surgical tool may be configured to separate tissue to create a tissue pocket sized to accept an implantable medical device. For example, the surgical tool may include a shaft defining a proximal end, a distal end, and a longitudinal axis. A handle may be coupled to the proximal end of the shaft, and the tool may also include one or more blades configured to move between a retracted configuration and a deployed configuration. In some examples, the one or more blades may be attached to the distal end of the shaft directly, via a hinge, or include hinge or configured to bend, such that the clinician may actuate a control that causes the one or more blades to move from the retracted configuration along the longitudinal axis to the deployed configuration which is extended away from the longitudinal axis. In other examples, the clinician may actuate a blade by moving the blade distally through a lumen along the longitudinal axis, past a curve at the distal end of the lumen, and out of an exit port formed in a side wall of the shaft.

The one or more blades may extend, in the deployed configuration, substantially perpendicular to the longitudinal axis at the distal end of the shaft. Substantially perpendicular blades may enable the one or more blades to move within a cutting plane in the tissue when rotated about the longitudinal axis. For example, by substantially perpendicular, the one or more blades may form an angle within 10 percent of a 90 degree angle (e.g., between 81 degrees and 99 degrees) to the longitudinal axis. In another example, substantially perpendicular indicates that the blades may form an angle within 5 percent of a 90 degree angle (e.g., between 85.5 degrees and 94.5 degrees) to the longitudinal axis. In another example, substantially perpendicular indicates that the blades may form an angle within 2 percent of a 90 degree angle (e.g., between 88.2 degrees and 91.8 degrees) to the longitudinal axis.

In some examples, the surgical tool may include graduated markings along a side wall of the shaft. The graduated markings may enable a clinician to see how much of the distal end of the shaft of the surgical tool has been inserted into the patient. In addition, or alternatively, the surgical tool may include a depth stop attached to the shaft. The depth stop may include a disk, one or more members, or other structure that extends radially outward from the shaft of the surgical tool. The depth stop may be set to a position that, when the distal surface of the depth stop contacts an external surface of skin of patient 14, the one or more blades will be at a specified depth when in the deployed configuration. The depth stop may be permanently attached to the shaft or configured to be adjusted via a screwed thread, ratcheting mechanism, or friction fit.

A clinician may use the surgical tool to create the tissue pocket at the desired location. For example, the clinician may insert a distal portion of shaft of the surgical tool into tissue of patient 14, where the shaft defining a distal end, a proximal end, and a longitudinal axis. The clinician may then move the one or more blades from the retracted configuration to the deployed configuration, wherein the one or more blades extend, in the deployed configuration, substantially perpendicular to the longitudinal axis at the distal end of the shaft. The clinician may also rotate the one or more blades in the deployed position to separate a first portion of tissue from a second portion of tissue such that IMD 16 is insertable between the first portion of tissue and the second portion of tissue. The clinician may rotate the entire surgical tool to rotate the one or more blades within the tissue. In other examples, the one or more blades may be rotatable via an inner shaft that rotates within an outer shaft to prevent rotational forces along the tissue next to the outer shaft.

The surgical tool may be constructed of one or more types of materials. Example materials may include one or more metals and/or metal alloys, one or more polymers, composite materials, or any other type of material. For example, the one or more blades may be constructed out of a polymer (e.g., nylon) or metal alloy (e.g., stainless steel) having an stiffness sufficient to cut through tissue during rotation of the blades. The surgical tool may be disposable or configured to be reused and sterilized between different patients.

Figure 3A:
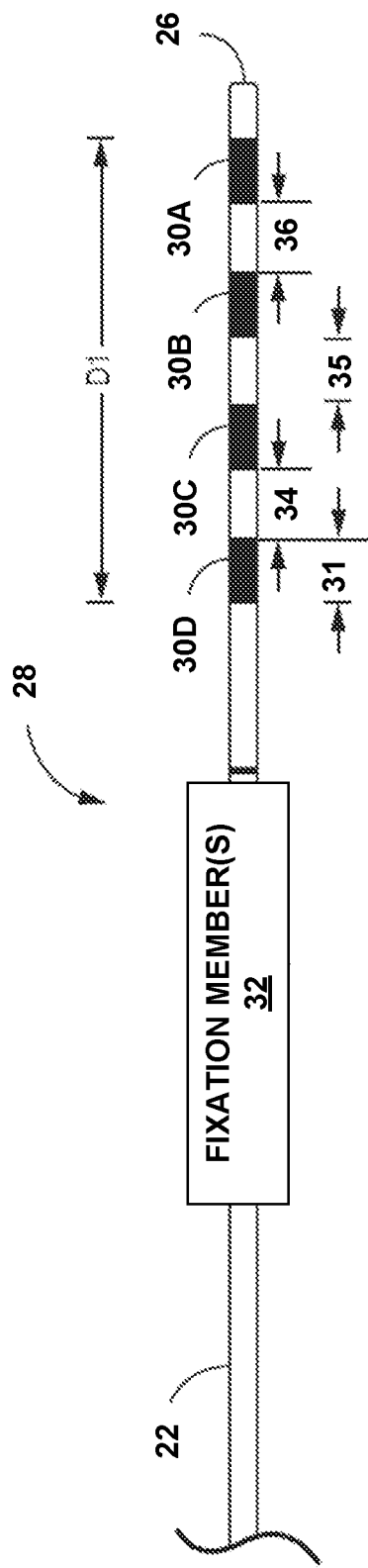
FIG. 3A is a conceptual diagram of a lead used for OSA therapy according to one or more examples.

FIG. 3A is a conceptual diagram of lead 20 used for OSA therapy according to one or more examples. For instance, FIG. 3A illustrates distal portion 28 of lead 20, where distal portion 28 of lead 20 may part of lead 20 that is implanted in tongue 40, as described above. Lead 20 may include one or more electrodes 30, and FIG. 3A shows lead 20 with four electrodes 30A, 30B, 30C, and 30D (collectively referred to as "electrodes 30") spaced apart longitudinally along lead body 22.

Lead body 22 may be a flexible lead body through which insulated electrical conductors extend to respective electrodes 30. The distal most electrode 30A may be adjacent or proximate to lead distal end 26. Each of electrodes 30 may be spaced proximally from the respective adjacent one of electrodes 30 by respective interelectrode distances 34, 35 and 36.

In some examples, each one of electrodes 30 may have equivalent electrode lengths 31. However, electrodes 30 may have electrode lengths 31 that are different from each other in order (e.g., to optimize placement of the electrodes 30 or the resulting electrical field of stimulation relative to targeted stimulation sites corresponding to left and right hypoglossal nerves or branches of hypoglossal nerves and/or motor points of protrusor muscles 42 and/or 46).

Spacing 34, 35, and 36 are shown to be approximately equal in FIG. 3A, however in other examples the interelectrode spacings 34, 35, and 36 may be different from each other (e.g., in order to optimize placement of electrodes 30 relative to the targeted stimulation sites). In some examples, electrodes 30A and 30B form an anode and cathode pair for delivering bipolar stimulation in one portion of the protrusor muscles 42 and/or 46 (e.g., either the left or right protrusor muscles or a proximal and/or distal portion of portion of the protrusor muscles). Electrodes 30C and 30D may form a second anode and cathode pair for delivering bipolar stimulation in a different portion of protrusor muscles 42 and/or 46 (e.g., the other of the left or right portions or the other of the proximal or distal portions). Accordingly, the interelectrode spacing 35 between the two bipolar pairs 30A, 30B and 30C, 30D may be different than the interelectrode spacing 34 and 36 between the anode and cathode within each bipolar pair 30A, 30B and 30C, 30D.

In some examples, housing 15 of IMD 16 may include an electrode that functions as cathode, and part of the anode and cathode pair with one of electrodes 30. In some examples, housing 15 itself may function as the cathode of an anode, cathode pair, with one of electrodes 30 forming the anode.

In one example, the total distance D1 encompassed by electrodes 30 along the distal portion 28 of lead body 22 may be about 20 millimeters, 25 millimeters, or 30 millimeters as examples. In one example, the total distance D1 is between 20 and 22 millimeters. The interelectrode spacings 34 and 36 within a proximal electrode pair 30C, 30D and a distal electrode pair 30A, 30B, respectively, may be 2 to 5 millimeters in some examples. The interelectrode spacing 35 separating the distal and proximal pairs 30A, 30B and 30C, 30D may be greater than the interelectrode spacings 34 and 36. For example, the interelectrode spacing 35 may be 4 to 6 millimeters in some examples. In one example, each of electrodes 30 has an electrode length 31 of 3 mm, and each of interelectrode spacings 34, 35 and 36 is 3 mm.

In FIG. 3A, each of electrodes 30 is a circumferential ring electrode which may be uniform in diameter with lead body 22. As described above, electrodes 30 may include other types of electrodes such as a tip electrode, a helical electrode, a coil electrode, a segmented electrode, a button electrode as examples. For instance, the distal most electrode 30A may be provided as a tip electrode at the lead distal end 26 with the remaining three electrodes 30B, 30C, and 30D being ring electrodes. In some examples, when electrode 30A is positioned at the distal end 26, electrode 30A may be a helical electrode configured to screw into the muscle tissue at the implant site to additionally serve as a fixation member for anchoring the distal portion 28 of lead 20 at the targeted therapy delivery site. In some examples, one or more of electrodes 30 may be a hook electrode or barbed electrode to provide active fixation of the distal portion 28 of lead 20 at the therapy delivery site.

Lead 20 may include one or more fixation members 32 for minimizing the likelihood of lead migration. Fixation member 32 may include multiple sets of tines which engage the surrounding tissue when lead distal portion 28 is positioned at the target therapy delivery site. The tines of fixation member 32 may extend radially and proximally at an angle relative to the longitudinal axis of lead body 22 to prevent or reduce retraction of lead body 22. Tines of fixation member 32 may be collapsible against lead body 22 when lead 20 is held within the confines of a lead delivery tool (e.g., a needle or introducer) used to deploy lead distal portion 28 at the target implant site. Upon removal of the lead delivery tool, the tines of fixation member 32 may spread to a normally extended position to engage with surrounding tissue and resist proximal and lateral migration of lead body 22. In some examples, fixation member 32 may additionally or alternatively include one or more hooks, barbs, helices, or other fixation mechanisms extending from one or more longitudinal locations along lead body 22 and/or lead distal end 26.

Fixation members 32 may partially or wholly engage one or more of protrusor muscles 42 and/or 46 and/or other muscles below tongue 40, and/or other soft tissues of the neck (e.g., fat and connective tissue), when proximal end of lead body 20 is tunneled to the tissue pocket of IMD 16 formed by a surgical tool described herein. In some examples, fixation member 32 may include one or more fixation mechanisms located at other locations, including at or proximate to distal end 26, between electrodes 30, or otherwise more distally or more proximally than the location shown in FIG. 3A.

The implant tissue pocket of IMD 16 may be created in a pectoral region of patient 14. Accordingly, the length of the elongated lead body 22 from distal portion 28 to the lead proximal end 24 may be selected to extend from a target therapy delivery site in protrusor muscles 42 and/or 46 to a location in the pectoral region where IMD 16 is implanted. The length may be up to 10 cm or up to 20 cm as examples but may generally be 25 cm or less, though longer or shorter lead body lengths may be used depending on the anatomy and size of patient 14.

Figure 3B:
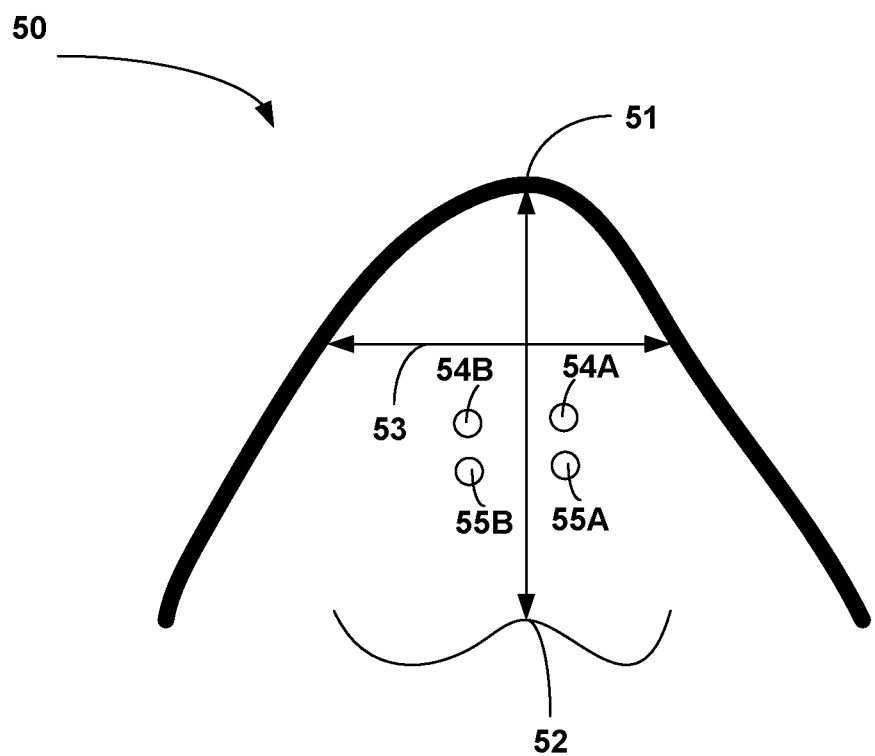
FIG. 3B is a conceptual diagram illustrating example locations of motor points where stimulation for OSA therapy may be delivered.

FIG. 3B is a conceptual diagram illustrating example locations of motor points where stimulation for OSA therapy may be delivered. FIG. 3B illustrates jaw 50 of patient 14, where patient 14 is in a supine position and jaw 50 of patient 14 is viewed from an inferior location of patient 14. For instance, FIG. 3B illustrates symphysis 51 and hyoid bone 52. In the example illustrated in FIG. 3B, the line interconnecting symphysis 51 and hyoid bone 52 may be considered as a y-axis along the midline of tongue 40. FIG. 3B also illustrates intergonial distance 53 between the two gonia of patient 14, where the gonia is a point on each side of the lower jaw 50 at the mandibular angle. Intergonial distance 53 may be along the x-axis of tongue 40.

FIG. 3B illustrates motor points 54A and 54B and motor points 55A and 55B. Motor points 54A may be motor points for the right genioglossus muscle, and motor points 54B may be motor points for the left genioglossus muscle. Motor points 55A may be motor points for the right geniohyoid muscle, and motor points 55B may be motor points for the left geniohyoid muscle. Motor points 54A and 54B and motor points 55A and 55B may genericize the motor points for each muscle for purposes of illustration. There may be additional motor points and/or motor points at different locations for each muscle.

In one or more examples, lead 20 and/or one or more electrodes 30 may be implanted proximate to motor points 54A, 54B, 55A, or 55B for stimulating at motor points 54A, 54B, 55A, and/or 55B. For instance, in examples where two leads are implanted, a first lead and its electrodes may be implanted proximate to motor points 54A and/or 55A and a second lead and its electrodes may be implanted proximate to motor points 54B and/or 55B. In one or more examples, electrodes 30 may be approximately 1 mm to 10 mm from respective motor points 54A, 54B, 55A, or 55B.

A hypoglossal nerve (e.g., on the left or right side of tongue 40) initially is a trunk of nerves fibers called axons. The axons of the hypoglossal nerve branch out. For example, the trunk of hypoglossal nerve includes multiple sets of axons including a first set of axons, and the first set of axons branch out from the trunk of the hypoglossal nerve. The first set of axons include multiple groups of axons including a first group of axons, and the first group of axons branch out from the first set of axons, and so forth. The locations where the branched-out axons interface with respective muscle fibers of protrusor muscles 42 and/or 46 (e.g., genioglossus and/or geniohyoid muscle) are referred to as motor points.

For instance, a branch of the hypoglossal nerve that interfaces (e.g., connects at the neuro-muscular junction) with the muscle fiber is referred to as a terminal branch, and the end of the terminal branch is a motor point. The length of a terminal branch may be approximately 10 mm from the hypoglossal nerve to the genioglossal or geniohyoid muscles. In some examples, there may be approximately an average of 1.5 terminal branches with a standard deviation of +0.7 for the right geniohyoid muscle, an average of 4.8 terminal branches with a standard deviation of +1.4 for the right genioglossus muscle, an average of 2.0 terminal branches with a standard deviation of +0.9 for the left geniohyoid muscle, and an average of 5.1 terminal branches with a standard deviation of +1.9 for the left genioglossus muscle.

There may be possible advantages with stimulating at motor points 54A, 54B, 55A, or 55B, as compared to some other techniques. For instance, some techniques utilize cuff electrodes or stimulate at the hypoglossal nerve. Due to the different bifurcation patterns, placing a cuff electrode around the hypoglossal nerve, or generally attaching an electrode to the hypoglossal nerve can be challenging. Also, where cuff electrodes or electrodes that attach to the hypoglossal nerve are used, implanting electrodes around or at each of the hypoglossal nerves requires multiple surgical entry points to attached to both hypoglossal nerves. Moreover, utilizing cuff electrodes or electrodes that attach to the hypoglossal nerves can possibly negatively impact the nerve by tugging, stretching, or otherwise causing irritation. Accordingly, utilizing lead 20 and electrodes 30 that are implanted proximate to the motor points may be beneficial (e.g., less surgery to implant and less impact on the nerve) as compared to techniques where cuff electrodes or electrodes implanted on the hypoglossal nerve are utilized.

Furthermore, stimulating at motor points 54A, 54B, 55A, and/or 55B, such as at the bifurcation point of a motor neuron that attach to muscle fibers, may provide advantages such as for better control of muscle movement. Because motor points 54A, 54B, 55A, and 55B are spatially distributed, by stimulating motor points 54A, 54B, 55A, and/or 55B, the amount of the genioglossus and geniohyoid muscle that is being stimulated can be controlled. Also, stimulating at motor points 54A, 54B, 55A, and/or 55B may allow for more gentle muscle activation. For instance, when stimulation is provided near the trunk of the hypoglossal nerve, even stimulation signal with relatively small amplitude can cause the genioglossus and/or geniohyoid muscle to fully protrude (e.g., there is high loop gain where small stimulation amplitudes cause large muscle protrusion). Fine tuning of how much to protrude the genioglossus and/or geniohyoid muscle may not be available when stimulating at a trunk of the hypoglossal nerve. However, there may be lower loop gain stimulating at motor points 54A, 54B, 55A, and/or 55B. For instance, a stimulation signal having a lower amplitude may move cause the genioglossus and/or geniohyoid muscle to protrude a small amount, and a stimulation signal having a higher amplitude may move cause the genioglossus and/or geniohyoid muscle to protrude a higher amount when stimulating at motor points 54A, 54B, 55A and/or 55B.

The following are example locations of motor points 54A, 54B, 55A, and 55B relative to the midline (x-axis), posterior symphysis 51 (y-axis), and depth (z-axis), where the depth is from the plane formed by the inferior border of symphysis 51 and anterior border of hyoid bone 52.

Motor points 54A may be for the right genioglossus muscle and may be located at 13.48 mm±3.59 from the x-axis, 31.01 mm±6.96 from the y-axis, and 22.58 mm±3.74 from the z-axis. Motor points 55A may be for the right geniohyoid muscle and may be located at 11.74 mm±3.05 from the x-axis, 41.81 mm±6.44 from the y-axis, and 16.29 mm±3.40 from the z-axis. Motor points 54B may be for the left genioglossus muscle and may be located at 9.96 mm±2.24 from the x-axis, 29.62 mm±9.25 from the y-axis, and 21.11 mm±4.10 from the z-axis. Motor points 55B may be for the left geniohyoid muscle and may be located at 11.45 mm±1.65 from the x-axis, 39.63 mm±8.03 from the y-axis, and 15.09 mm±2.41 from the z-axis.

Figure 4:
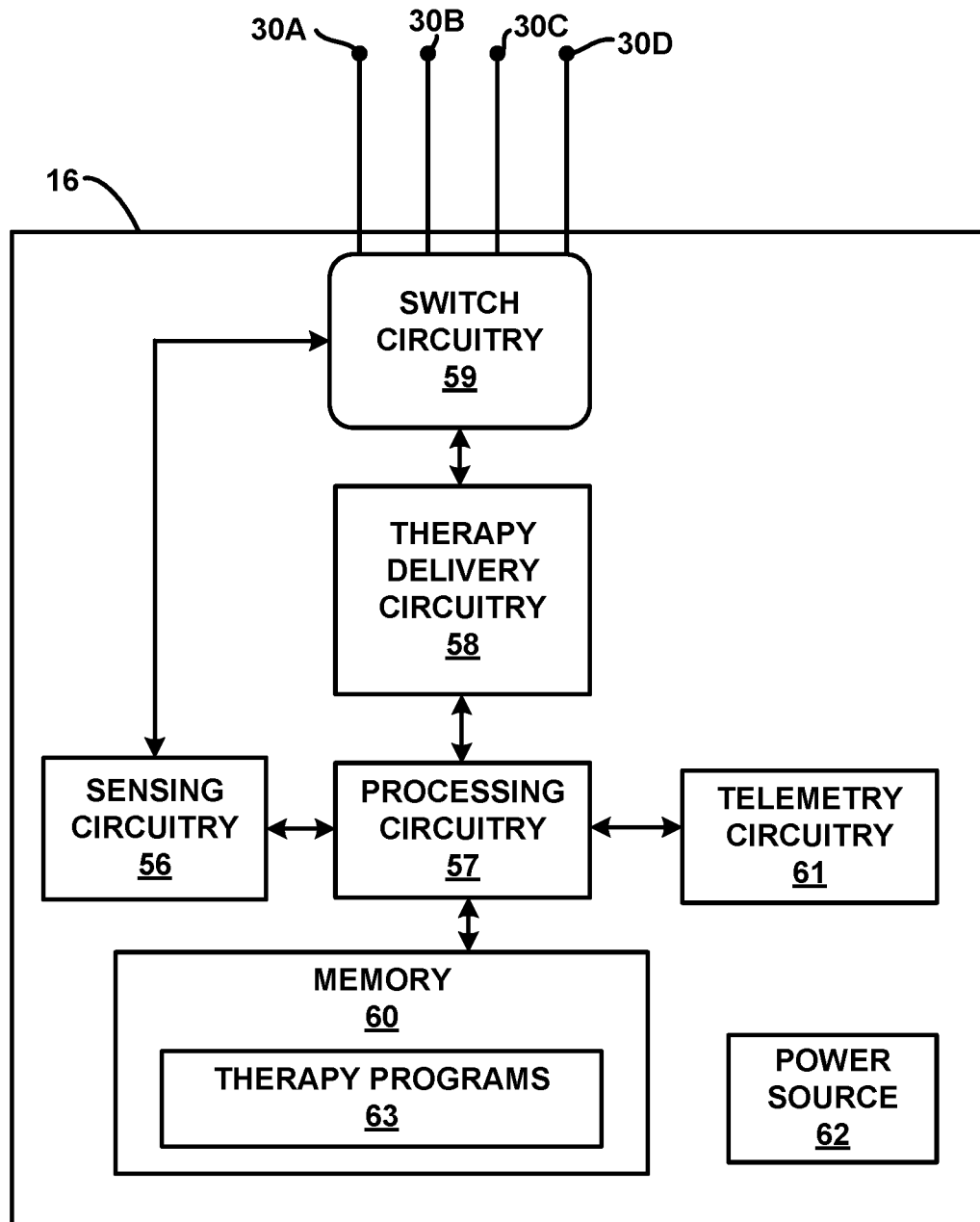
FIG. 4 is block diagram illustrating example configurations of implantable medical devices (IMDs) which may be utilized in the system of FIG. 1.

FIG. 4 is block diagram illustrating example configurations of implantable medical devices (IMDs) which may be utilized in the system of FIGS. 1 and 2. As shown in FIG. 4, IMD 16 includes sensing circuitry 56, processing circuitry 57, therapy delivery circuitry 58, switch circuitry 59, memory 60, telemetry circuitry 61, and power source 62. IMD 16 may include a greater or fewer number of components. For example, in some examples, such as examples in which IMD 16 deliver the electrical stimulation in an open-loop manner, IMD 16 may not include sensing circuitry 56.

Switch circuitry 59 may be configured to, in response to instructions from processing circuitry 57, switch the coupling of electrodes 30 between sensing circuitry 56 and therapy delivery circuitry 58. In examples where sensing circuitry 56 is not used, switch circuitry 59 may not be needed. However, even in examples where sensing circuitry 56 is not used, IMD 16 may include switch circuitry 59 such as to disconnect electrodes 30 from therapy delivery circuitry 58.

Although not shown in FIG. 4, in some examples, IMD 16 may include one or more sensors configured to sense posture or position of patient 14. For example, IMD 16 may include accelerometer to determine if patient 14 is lying down. Another example of the one or more sensors is a motion sensor, and movement sensed by the motion sensor may indicate if patient 14 is having restless sleep, which may be indicative of the onset of OSA. Additional examples of the sensors include acoustical sensors or a microphone for detecting vibrations in upper airway 48. Vibrations in upper airway 48 may be indicative of the onset of OSA. In some examples, processing circuitry 57 may control delivery of therapy based on information received from the one or more sensors, such as delivery therapy after sensing an onset of OSA.

In some examples, electrodes 30 may be configured to sense electromyogram (EMG) signals. Sensing circuitry 56 may be switchably coupled to electrodes 30 via switch circuitry 59 to be used as EMG sensing electrodes with electrodes 30 are not being used for stimulation. EMG signals may be used by processing circuitry 57 to detect sleep state and/or low tonal state of protrusor muscles 42 and/or 46 for use in delivering electrical stimulation. In some examples, rather than using electrodes 30 or in addition to using electrodes 30, there may be other electrodes or sensors used to sense EMG signals.

In general, IMD 16 may comprise any suitable arrangement of hardware, alone or in combination with software and/or firmware, to perform the techniques attributed to IMD 16 and processing circuitry 57, therapy delivery circuitry 58, and telemetry circuitry 61 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 16 also, in various examples, may include a memory 60, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although sensing circuitry 56, processing circuitry 57, therapy delivery circuitry 58, switch circuitry 59, and telemetry circuitry 61 are described as separate circuitry, in some examples, sensing circuitry 56, processing circuitry 57, therapy delivery circuitry 58, switch circuitry 59, and telemetry circuitry 61 are functionally integrated. In some examples, sensing circuitry 59, processing circuitry 57, therapy delivery circuitry 58, switch circuitry 59, and telemetry circuitry 61 correspond to individual hardware units, such as ASICs, DSPs, FPGAs, or other hardware units.

Memory 60 stores therapy programs 63 that specify stimulation parameter values for the electrical stimulation provided by IMD 16. Memory 60 may also store instructions for execution by processing circuitry 57, in addition to stimulation programs 63. Information related to sensed parameters of patient 14 (e.g., from sensing circuitry 56 or the one or more sensors of IMD 16) may be recorded for long-term storage and retrieval by a user, and/or used by processing circuitry 57 for adjustment of stimulation parameters (e.g., amplitude, pulse width, and pulse rate). In some examples, memory 60 includes separate memories for storing instructions, electrical signal information, and stimulation programs 63. In some examples, processing circuitry 57 may select new stimulation parameters for a stimulation program 63 or new stimulation program from stimulation programs 63 to use in the delivery of the electrical stimulation based on patient input and/or monitored physiological states after termination of the electrical stimulation.

Generally, therapy delivery circuitry 58 generates and delivers electrical stimulation under the control of processing circuitry 57. In some examples, processing circuitry 57 controls therapy delivery circuitry 58 by accessing memory 60 to selectively access and load at least one of stimulation programs 63 to therapy delivery circuitry 58. For example, in operation, processing circuitry 57 may access memory 60 to load one of stimulation programs 63 to therapy delivery circuitry 57.

By way of example, processing circuitry 57 may access memory 60 to load one of stimulation programs 63 to therapy delivery circuitry 58 for delivering the electrical stimulation to patient 14. A clinician or patient 14 may select a particular one of stimulation programs 63 from a list using a programming device, such as a patient programmer or a clinician programmer. Processing circuitry 57 may receive the selection via telemetry circuitry 61. Therapy delivery circuitry 58 delivers the electrical stimulation to patient 14 according to the selected program for an extended period of time, such as minutes or hours while patient 14 is asleep (e.g., as determined from the one or more sensors and/or sensing circuitry 56). For example, processing circuitry 57 may control switch circuitry 59 to couple electrodes 30 to therapy delivery circuitry 58.

Therapy delivery circuitry 58 delivers electrical stimulation according to stimulation parameters. In some examples, therapy delivery circuitry 58 delivers electrical stimulation in the form of electrical pulses. In such examples, relevant stimulation parameters may include a voltage amplitude, a current amplitude, a pulse rate, a pulse width, a duty cycle, or the combination of electrodes 30 that therapy delivery circuitry 58 uses to deliver the stimulation signal. In some examples, therapy delivery circuitry 58 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 30 therapy delivery circuitry 58 uses to deliver the stimulation signal.

Processing circuitry 56 may select stimulation programs 63 for alternating delivery of electrical stimulation between stimulating the left protrusor muscles 42 and/or 46 and the right protrusor muscles 42 and/or 46, such as in examples where two leads 20 are implanted. In some examples, there may be some overlap in the delivery of electrical stimulation such that for some of amount of time both left and right protrusor muscles 42 and/or 46 are being stimulated. In some examples, there may be a pause in alternating stimulation (e.g., stimulate left protrusor muscles, a time period with no stimulation, then stimulate right protrusor muscles, and so forth). Processing circuitry 56 may also select stimulation programs 63 that select between different combinations of electrodes 30 for stimulating, such as to stimulate different locations of the hypoglossal nerve(s) and/or motor points, which may help with fatigue as well as provide more granular control of how much to protrude tongue 40.

In the example of FIG. 4, therapy delivery circuitry 58 drives electrodes 30 of lead 20. Specifically, therapy delivery circuitry 58 delivers electrical stimulation to tissue of patient 14 via selected electrodes 30A-30D carried by lead 20. A proximal end of lead 20 extends from the housing of IMD 16 and a distal end of lead 20 extends to a target therapy site, such as one or both hypoglossal nerves and/or motor points 54A, 55A, 54B, and/or 55B. Therapy delivery circuitry 58 may deliver electrical stimulation with electrodes on more than one lead and each of the leads may carry one or more electrodes, such as when patient 14 is implanted with two leads 20 in tongue 40 for stimulating both hypoglossal nerves simultaneously or bilaterally (e.g., one after the other) or both motor points 54A and 54B and/or motor points 55A and 55B. The leads may be configured as an axial lead with ring electrodes or segmented electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 16.

In some examples, processing circuitry 57 may control therapy delivery circuitry 58 to deliver or terminate the electrical stimulation based on patient input received via telemetry circuitry 61. Telemetry circuitry 61 includes any suitable hardware, firmware, software or any combination thereof for communicating with another device, such as an external programmer. Under the control of processing circuitry 57, telemetry circuitry 61 may receive downlink telemetry (e.g., patient input) from and send uplink telemetry (e.g., an alert) to a programmer with the aid of an antenna, which may be internal and/or external. Processing circuitry 57 may provide the data to be uplinked to the programmer and the control signals for telemetry circuitry 61 and receive data from telemetry circuitry 61.

Generally, processing circuitry 57 controls telemetry circuitry 61 to exchange information with a medical device programmer and/or another device external to IMD 16. Processing circuitry 57 may transmit operational information and receive stimulation programs or stimulation parameter adjustments via telemetry circuitry 61. Also, in some examples, IMD 16 may communicate with other implanted devices, such as stimulators, control devices, or sensors, via telemetry circuitry 61.

Power source 62 delivers operating power to the components of IMD 16. Power source 62 may include a battery and a power generation circuit to produce the operating power. In some examples, the battery may be rechargeable to allow extended operation. Recharging may be accomplished through proximal inductive interaction (e.g., inductive coupling) between an external charger (that includes a primary inductive coil) and a secondary inductive charging coil within IMD 16. In some examples, programmer 70 may include the primary inductive charger to operate as the external charger. In other examples, the external charger may be a separate device configured to transfer power to IMD 16. In this manner, the primary inductive coil of the external charger may generate a magnetic field that is directed into tissue towards IMD 16. The magnetic field may then induce an electrical current within the secondary indictive coil of the IMD 16. Since the magnetic field may be tuned to have a certain field strength at a particular distance, and the secondary coil may be tuned to generate a current according to a particular field strength, a certain distance between the IMD 16 and external charger may generate electrical current at a desired efficiency and, in some examples, reduced heating of IMD 16 from the magnetic field. In this manner, the surgical tools described herein may be set to create the tissue pocket at a depth in tissue such that the tissue thickness between IMD 16 and the external charger promotes the desired charging efficiency. In other examples, an external inductive power supply may transcutaneously power IMD 16 whenever electrical stimulation is to occur.

Figure 5:
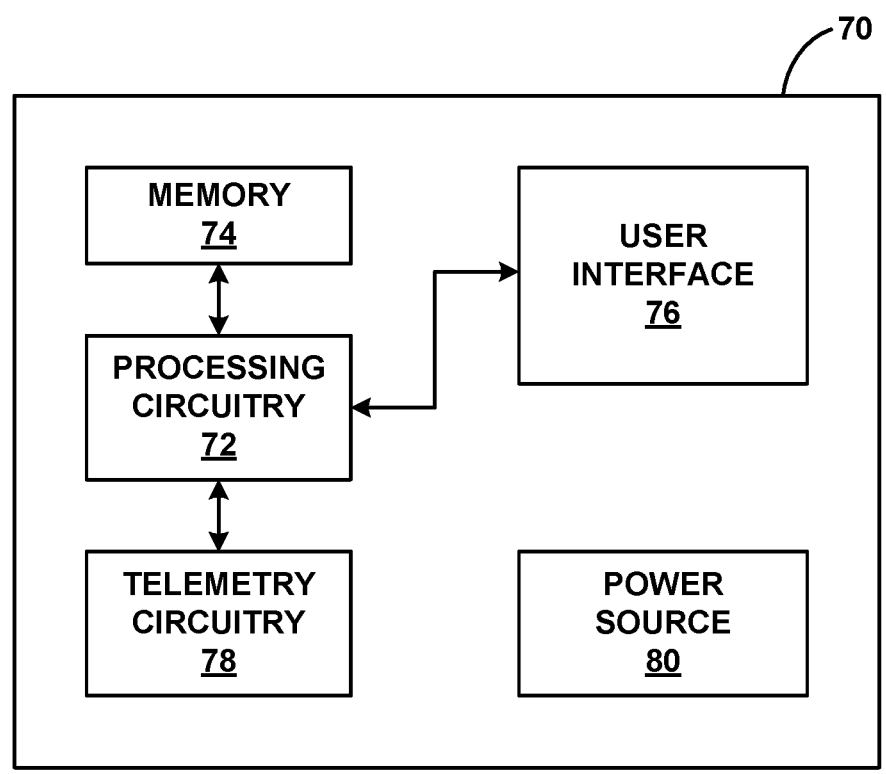
FIG. 5 is a block diagram illustrating an example configuration of an external programmer.

FIG. 5 is a block diagram illustrating an example configuration of an external programmer 70 shown in FIG. 1.

While programmer 70 may generally be described as a hand-held computing device, the programmer may be a notebook computer, a cell phone, or a workstation, for example. As illustrated in FIG. 5, external programmer 70 may include processing circuitry 72, memory 74, user interface 76, telemetry circuitry 78, and power source 80.

In general, programmer 70 comprises any suitable arrangement of hardware, alone or in combination with software and/or firmware, to perform the techniques attributed to programmer 70, and processing circuitry 72, user interface 76, and telemetry module 78 of programmer 70. Examples of processing circuitry 72 may include one or more processors, such as one or more microprocessors, DSPs, ASICs, FPGAs, or any other equivalent integrated or discrete logic circuitry, as well as any combinations of such components. Examples of memory 74 include RAM, ROM, PROM, EPROM, EEPROM, flash memory, a hard disk, a CD-ROM, comprising executable instructions for causing the one or more processors to perform the actions attributed to them. Moreover, although processing circuitry 72 and telemetry circuitry 78 are described as separate circuitry, in some examples, processing circuitry 72 and telemetry circuitry 78 are functionally integrated. In some examples, processing circuitry 72 and telemetry circuitry 78 correspond to individual hardware units, such as ASICs, DSPs, FPGAs, or other hardware units.

In some examples, memory 74 may further include program information (e.g., stimulation programs) defining the electrical stimulation, similar to those stored in memory 60 of IMD 16. The stimulation programs stored in memory 74 may be downloaded into memory 60 of IMD 16.

User interface 76 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processing circuitry 72 may present and receive information relating to electrical stimulation and resulting therapeutic effects via user interface 76. For example, processing circuitry 72 may receive patient input via user interface 76. The input may be, for example, in the form of pressing a button on a keypad or selecting an icon from a touch screen.

Processing circuitry 72 may also present information to the patient in the form of alerts related to delivery of the electrical stimulation to patient 14 or a caregiver via user interface 76. Although not shown, programmer 70 may additionally or alternatively include a data or network interface to another computing device, to facilitate communication with the other device, and presentation of information relating to the electrical stimulation and therapeutic effects after termination of the electrical stimulation via the other device.

Telemetry circuitry 78 supports wireless communication between IMD 16 and programmer 70 under the control of processing circuitry 72. Telemetry circuitry 78 may also be configured to communicate with another computing device via wireless communication techniques, or direct communication through a wired connection. In some examples, telemetry circuitry 78 may be substantially similar to telemetry circuitry 61 of IMD 16 described above, providing wireless communication via an RF or proximal inductive medium. In some examples, telemetry circuitry 61 may include an antenna, which may take on a variety of forms, such as an internal or external antenna. In some examples, the depth of the tissue pocket created by the surgical tool may be set to promote efficient telemetry between telemetry circuitry 78 of computing device 70 and telemetry circuitry 61 of IMD 16.

Examples of local wireless communication techniques that may be employed to facilitate communication between programmer 70 and another computing device include RF communication according to the 802.11 or Bluetooth specification sets, infrared communication (e.g., according to the IrDA standard), or other standard or proprietary telemetry protocols. In this manner, other external devices may be capable of communicating with programmer 70 without needing to establish a secure wireless connection.

Power source 80 delivers operating power to the components of programmer 70. Power source 80 may include a battery and a power generation circuit to produce the operating power. In some examples, the battery may be rechargeable to allow extended operation. As discussed above with respect to FIG. 4, programmer 70 may include a primary coil or other components configured to transfer power wirelessly to IMD 16 or other implantable devices. As discussed herein, power transfer may be most efficient at a particular depth or within a certain distance between the external charger and IMD 16.

It should be noted that system 10, and the techniques described herein, may not be limited to treatment or monitoring of a human patient. In alternative examples, system 10 may be implemented in non-human patients, e.g., primates, canines, equines, pigs, and felines. These other animals may undergo clinical or research therapies that my benefit from the subject matter of this disclosure. Various examples are described herein, such as the following examples.

Figure 6A:
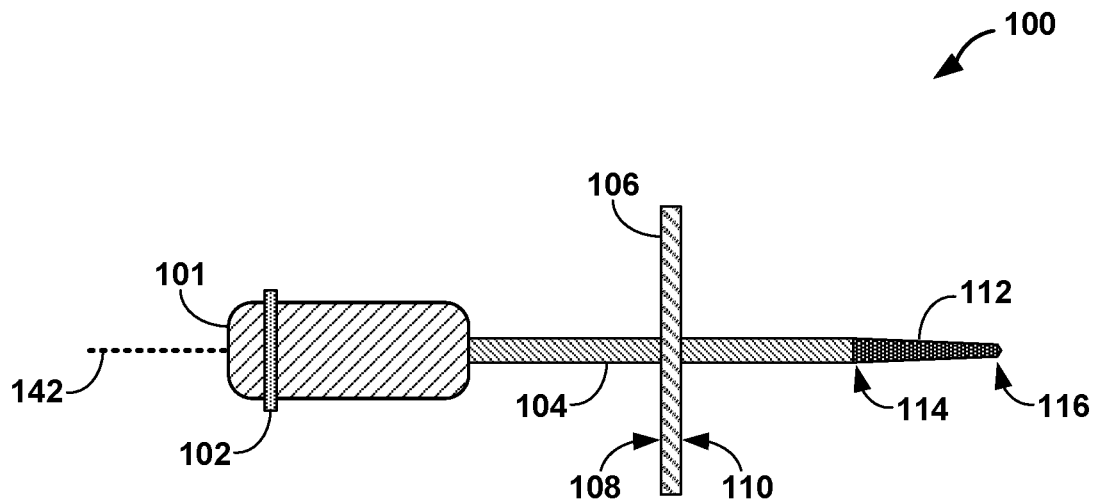
FIGS. 6A and 6B are side and perspective views of an example surgical tool for creating a pocket within tissue for implanting a medical device.
Figure 6B:
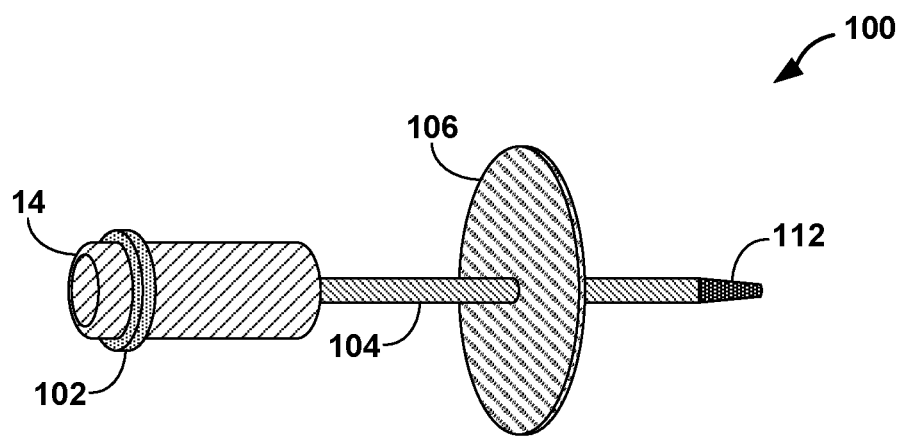

FIGS. 6A and 6B are side and perspective views of an example surgical tool 100 configured to create a pocket within tissue for IMD 16. Surgical tool 100 is shown in the retracted configuration in both of FIGS. 6A and 6B. As shown in FIG. 6A, surgical tool 100 includes handle 101 attached to a proximal end of shaft 104. Proximal end 114 of blade 112 is attached to (e.g., directly or indirectly coupled to) the distal end of shaft 114, either via a hinge or directly to shaft 114. Blade tip 116 is at the distal end of blade 112.

Depth stop 106 is disposed at an axial position along shaft 104. Depth stop 106 includes a proximal side 108 and a distal side 110, where the distal side 110 is configured to contact an external surface of skin of a patient. Since depth stop 106 is configured to remain external from the patient, insertion of shaft 104 and blade 112 into the tissue stops once distal side 110 of depth stop 106 contacts the skin. In this manner, depth stop 106 may be disposed at an axial position along shaft 104 and configured to contact skin and prevent shaft 104 and blade 112 from being inserted further into tissue. In some examples, depth stop 104 may be permanently attached to an outer surface of shaft 104 such that the distance between distal side 110 and the deployed configuration of blade 112 (e.g., approximately proximal end 114 of blade 112), is appropriate for implantation of IMD 16.

In other examples, depth stop 106 may be adjustable to different axial positions along shaft 104. For example, depth stop 106 and shaft 104 may have a threaded connection. An inner surface of depth stop may be define a helical structure that is matched to a helical structure of shaft 104 such that rotation of depth stop 106 with respect to shaft 104 may change the axial position of depth stop 106. In another example, depth stop 106 may have a ratcheted connection to shaft 104. In other example, depth stop 106 may form a friction fit to shaft 104 that is movable. In any of these or other adjustable connections, a clinician or other operator may adjust the axial position of depth stop 106 to create a desired depth of tissue to the tissue pocket. In this manner, depth stop 106 may be configured to move from a first axial position to a second axial position along shaft 104.

In the example of FIGS. 6A and 6B, depth stop 106 is shown as a planar disk. The disk may have a first radius at least half of a second radius of the one or more blades in the deployed configuration. In some examples, the radius of the disk may be between approximately 0.5 cm and 20 cm. In other examples, the radius of the disk may be between approximately 2.0 cm and 10 cm. In other examples, depth stop 106 may have a conical shape with the outer edges of the conical shape directed towards the blade 112. In another example, depth stop 106 may include one or more arms that extend radially outward from shaft 104. In any case, depth stop 106 may be a physical barrier that prevents blade 112 from being inserted further into the tissue.

Control 102 is included with handle 102. Control 102 may be a ring or disk that rotates about longitudinal axis 142. Control 102 may be coupled to an internal shaft or cable, through a lumen of shaft 104, that is coupled to blade 112 or a fixture that holds blade 112. For example, rotation of control 102 may, through a threaded connection to the internal shaft, move the internal shaft within shaft 104 and cause blade 112 to change from the retracted configuration to the deployed configuration. In one example, blade 112 is attached to the distal end of shaft 104 via a hinge, where the hinge is configured move the blade 112 between the retracted configuration and the deployed configuration. For example, rotation of control 102 may cause the internal shaft mechanically coupled to proximal end 114 of blade 112 to pivot at the hinge. The hinge may be configured for allow blade 112 to move within a single plane in some examples. In other examples, tool 100 may not include a hinge. Instead, actuation of control 102 may cause blade 112 to flex, or bend, at proximal end 114 until blade tip 116 is extended substantially perpendicular from longitudinal axis 142 and the side wall of shaft 104.

In one example, blade 112 may include at least one beveled edge configured to cut tissue. The beveled edge of blade 112 may be disposed along the length of the blade to enable the beveled edge to cut tissue when blade 112 is rotated about longitudinal axis 142 in the deployed configuration. In other examples, blade 112 may have beveled edges along both lengths of the blade. In addition, or alternatively, blade tip 116 may include a beveled edge or a point to blade 112.

In some examples, the length (e.g., the distance from the proximal end 114 to blade tip 116) is between approximately 0.5 cm and 10.0 cm. In another example, the length of blade 112 may be between approximately 1.0 cm and 8.0 cm. In other examples, the length of blade 112 may be between approximately 2.0 cm and 5.0 cm. In other examples, the length of blade 112 may be less than 0.5 cm or greater than 10.0 cm. The length of blade 112 may be greater than a width of blade 112. The width of blade 112 may be the distance along the blade in the direction of the hinged axis, in the examples in which a hinge attaches blade 112 to shaft 104. In some examples, blade 112 is a rectangular shape. In other examples, blade 112 may have a triangular, trapezoidal, or curved shape in which the width of blade tip 116 is wider than the width of proximal end 114. In some examples, the distal edge of blade tip 116 may be curved. Blade 112 also defines a thickness that is the dimension of blade 112 along the longitudinal axis when blade 112 is in the deployed configuration. The width is generally greater than the thickness of blade 112. Although a single blade 116 is shown in FIG. 6A, tool 100 may include two or more blades in other examples. Multiple blades may be fanned out, as discussed in FIGS. 15A and 15B.

Blade 112 is shown with a single solid body, such that rotation of blade 112 through tissue will create a single cut that separates two portions of tissue. In other examples, blade 112 may have different shapes. For example, blade 112 may have a loop or hollow box shape configured to remove a volume of tissue. For example, such a hollow box shape may rotate through tissue to remove a disk-shaped volume of tissue. This disk-shaped volume of tissue may be sized similar to IMD 16.

Figure 7:
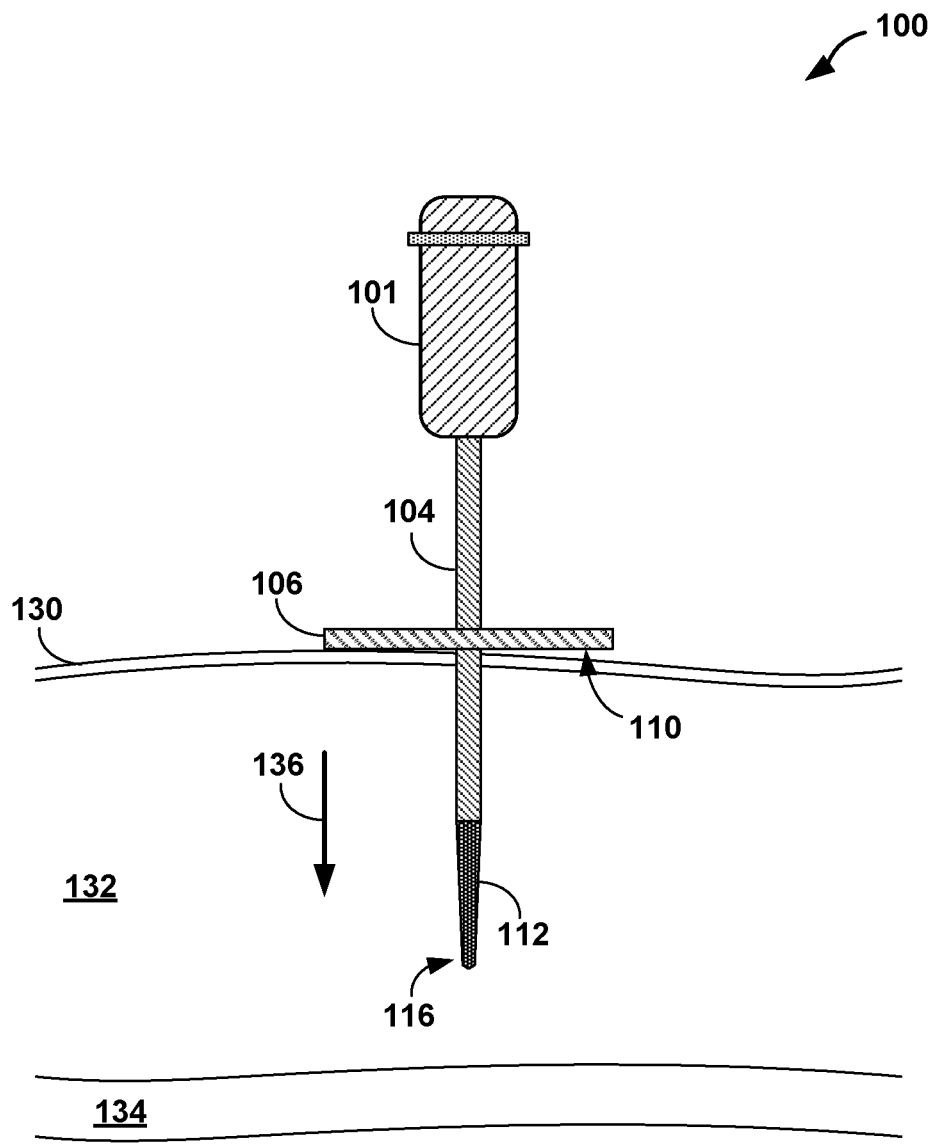
FIGS. 7, 8, 9A, 9B, and 10 are conceptual diagrams illustrating an example procedure for creating a tissue pocket with a surgical tool described herein.

FIGS. 7, 8, 9A, 9B, and 10 are conceptual diagrams illustrating an example procedure for creating tissue pocket 160 with surgical tool 100. As shown in FIG. 7, a clinician may insert blade tip 116 through an opening in skin 130. Blade tip 116 may be configured to pierce skin 130. In other examples, the clinician creates an incision in skin 130 prior to inserting blade tip 116. The clinician, while holding handle 101, may push blade 112 in the retracted configuration and shaft 104 into adipose tissue 132 in the direction of arrow 136. Deep of adipose tissue 132 may be connective tissue 134, such as bone or muscle. Once distal surface 110 of depth stop 106 contacts the exterior surface of skin 130, the clinician will not be able to push tool 100 any further into adipose tissue 132. At this point, the clinician may move blade 112 from the retracted configuration into the deployed configuration.

Figure 8:
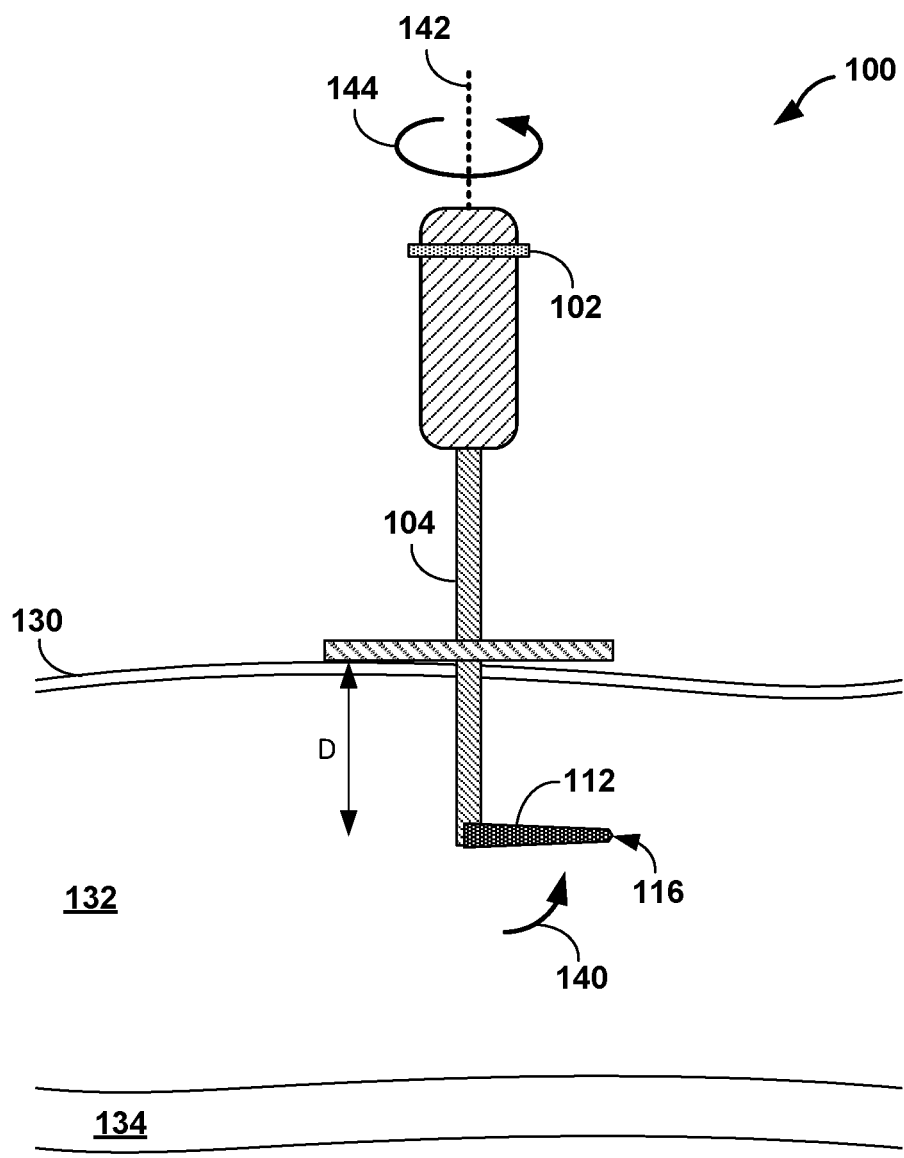

As shown in FIG. 8, the clinician has rotated control 102 about longitudinal axis 142 in the direction of arrow 144 in order to flex blade 116 in the direction of arrow 140. In the deployed configuration, blade 112 is oriented such that the length of blade 112 is approximately set to the depth D specified for the IMD 16. As discussed above, depth stop 106 is disposed at the appropriate axial position along shaft 104 such that blade 112 is set to depth D when in the deployed configuration. Although moving blade 112 through adipose tissue 132 in the direction of arrow 140 may cause some trauma to the tissue in this area, the disturbance may not affect the implantation of the IMD 16.

Figure 9A:
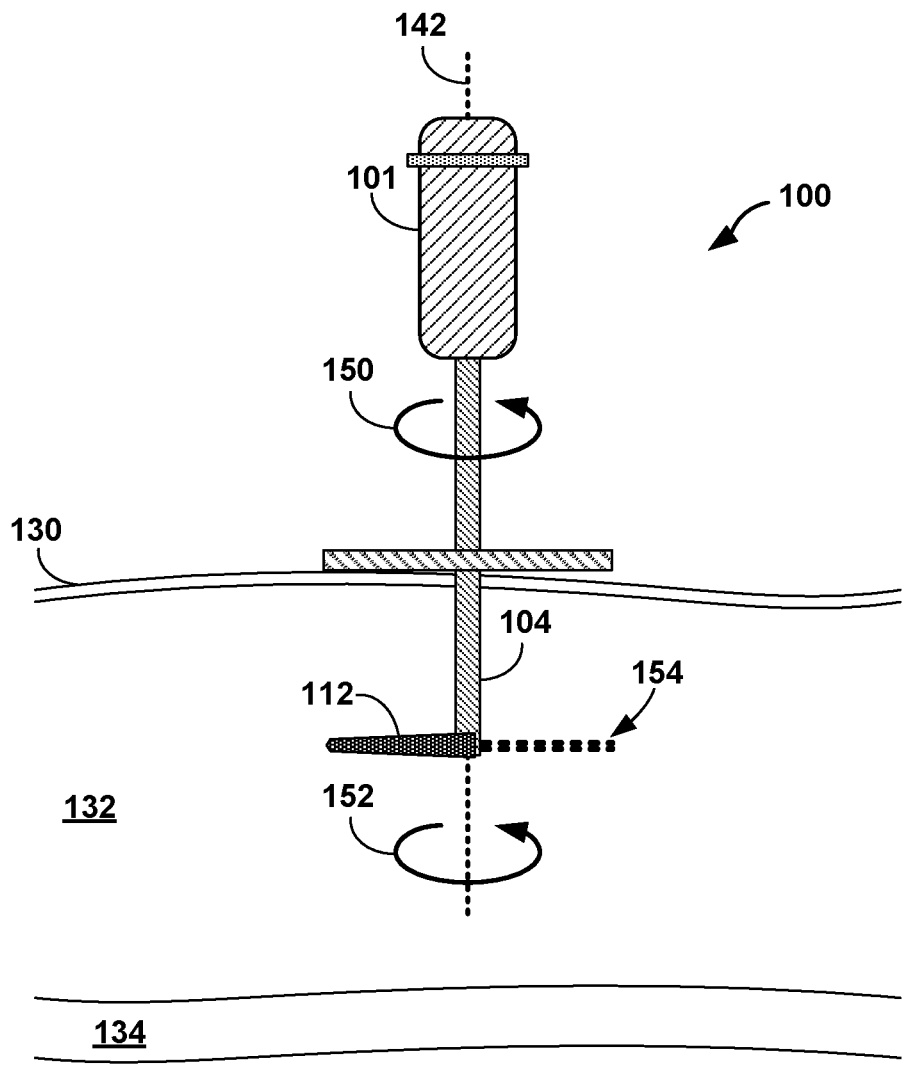

As shown in FIG. 9A, the clinician may rotate blade 112 in the deployed configuration. Once blade 112 is in the deployed configuration, blade 112 may be positioned in a plane orthogonal to longitudinal axis 142. The clinician may hold handle 101 and rotate handle 101 in the direction of arrow 150 about longitudinal axis 142. Rotation of handle 101 also rotates shaft 104, which rotates blade 112 about longitudinal axis 142 in the direction of arrow 152. In some examples, blade 112 may be rotated in either direction about longitudinal axis 142. In other examples, blade 112 may be rotated in a single direction. For example, only one edge of blade 112 may have a beveled or cutting edge. Rotation of blade 112 through adipose tissue 132 creates cut 154. Cut 154 indicates the separation between portions of tissue 132 that has been created by blade 112.

Figure 9B:
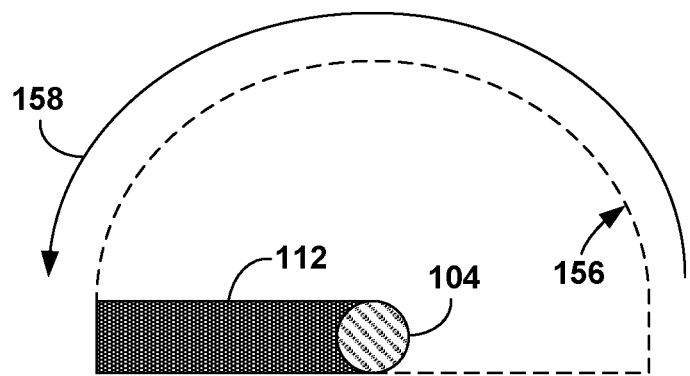

FIG. 9B is a bottom view of tool 100 in FIG. 9A. Since blade 112 has been rotated approximately 180 degrees about longitudinal axis 142 in the direction of arrow 158, path 156 indicates the extend of cut 154 at this point in the rotation. As the clinician continues to rotate blade 112 through adipose tissue 132, the cut 154 increases in size, e.g., increases the circumferential magnitude of cut 154. Once the leading edge of blade 112 moves 360 degrees about longitudinal axis 142, a disk-shaped cut will have been formed in adipose tissue 132. In some examples, the clinician may rotate blade 112 further than 360 degrees, or more than one turn, to ensure that the cut 154 is complete for the tissue pocket.

In other examples, blade 112 may be rotated about longitudinal axis 142 using an inner shaft that is coupled to blade 112 and rotated within shaft 104. In this manner, handle 101, or a different control, may be configured to rotate blade 112 without shaft 104 moving with respect to the surrounding tissue. The inner shaft within a lumen of shaft 104 may rotate freely within shaft 104 about longitudinal axis 142.

Figure 10:
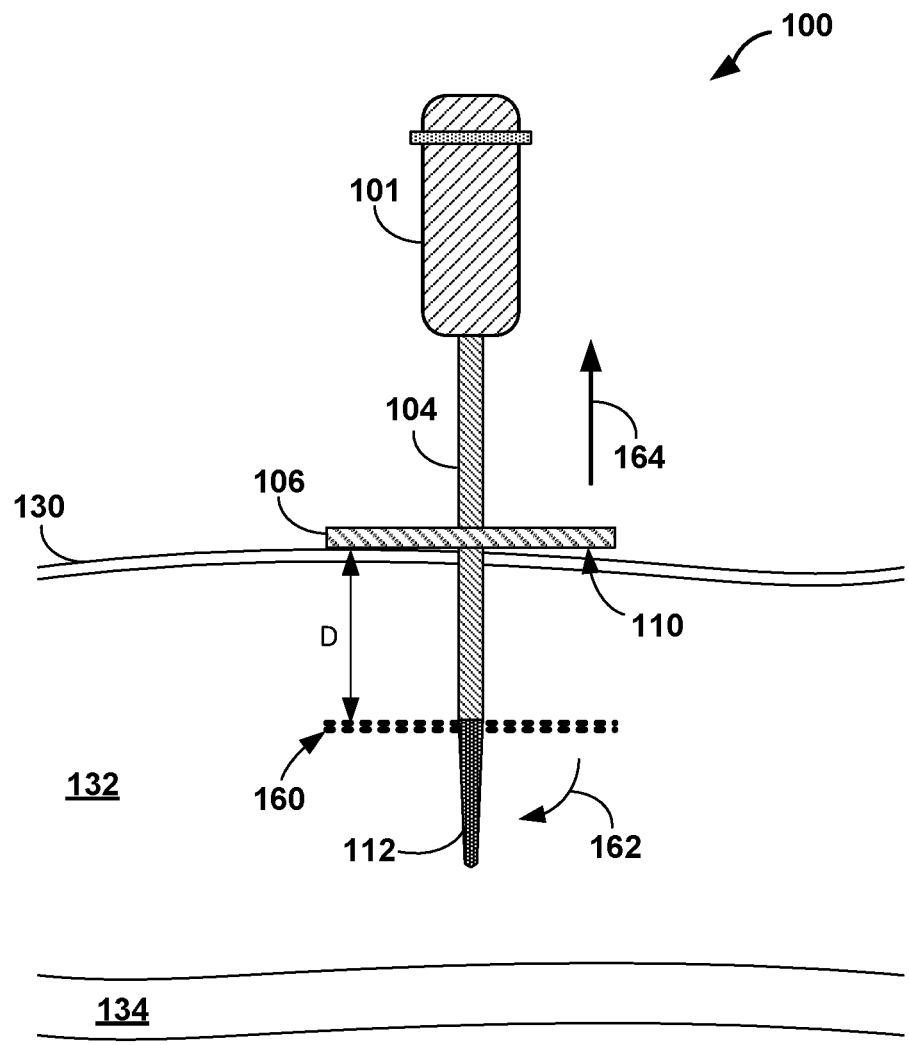

As shown in FIG. 10, blade 112 has completed separating tissue 132 to form tissue pocket 160. Then, the clinician can move blade 112 in the direction of arrow 162 back to the retracted configuration. Once in the retracted configuration, the clinician can pull out on handle 101 in the direction of arrow 164 and remove surgical tool 101 from adipose tissue 132 and skin 130.

Figure 11:
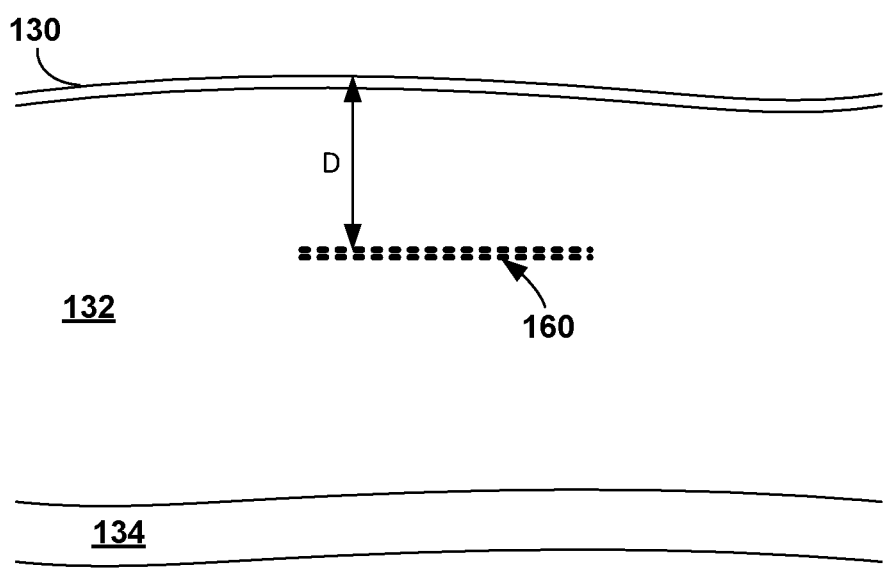
FIG. 11 is a conceptual diagram illustrating an example separation in tissue created by a surgical tool.

FIG. 11 is a conceptual diagram illustrating an example separation in tissue created by example surgical tool 100. As shown in FIG. 11, tissue pocket 160 has been created in adipose tissue 132 at a depth D from the exterior surface of skin 130. Although not shown in FIG. 11, an incision or other opening may be present between tissue pocket 160 and skin 130. This incision may be from insertion of surgical tool 100 and/or in preparation of inserting an IMD, such as IMD 16 or IMD 170 of FIG. 12.

Figure 12:
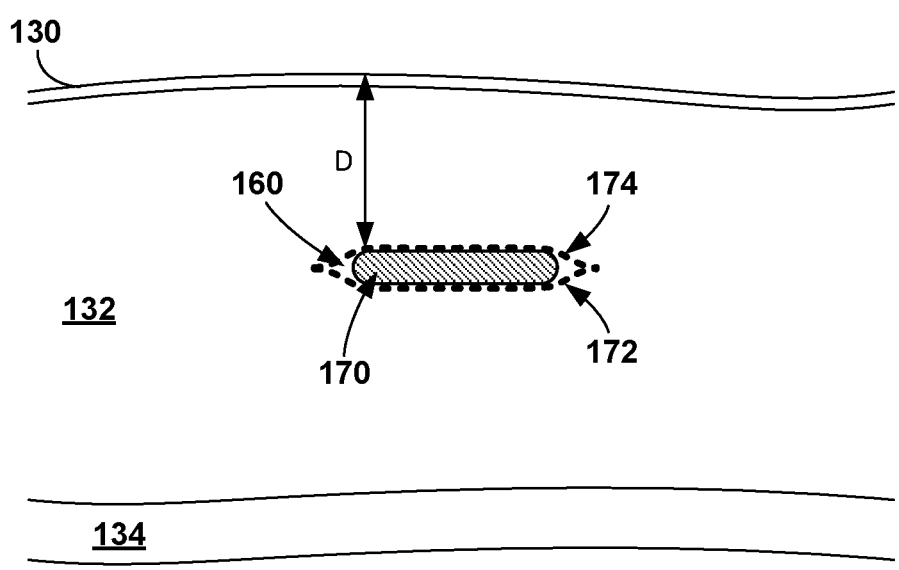
FIG. 12 is a conceptual diagram illustrating an example implantable medical device implanted in a pocket between portions of separated tissue.

As shown in FIG. 12, IMD 170 has been inserted into tissue pocket 160 formed by surgical tool 100. IMD 170 may be an example of IMD 16 or any other type of IMDs. When inserted into tissue pocket 160, IMD 170 is contacted by superficial tissue surface 174 on one side and deep tissue surface 172 on the other side. Together, superficial tissue surface 174 and deep tissue surface 172 forms tissue pocket 160. The depth D may correspond to the thickness of adipose tissue 132 and skin 130 between superficial tissue surface 174 and the exterior surface of skin 130. The depth D may depend on the type of IMD 170 and/or the surrounding anatomy of patient 14. Depth D may be between approximately 0.1 cm and 5.0 cm in some examples. In other examples, depth D may be between approximately 1.0 cm and 3.0 cm.

Figure 13:
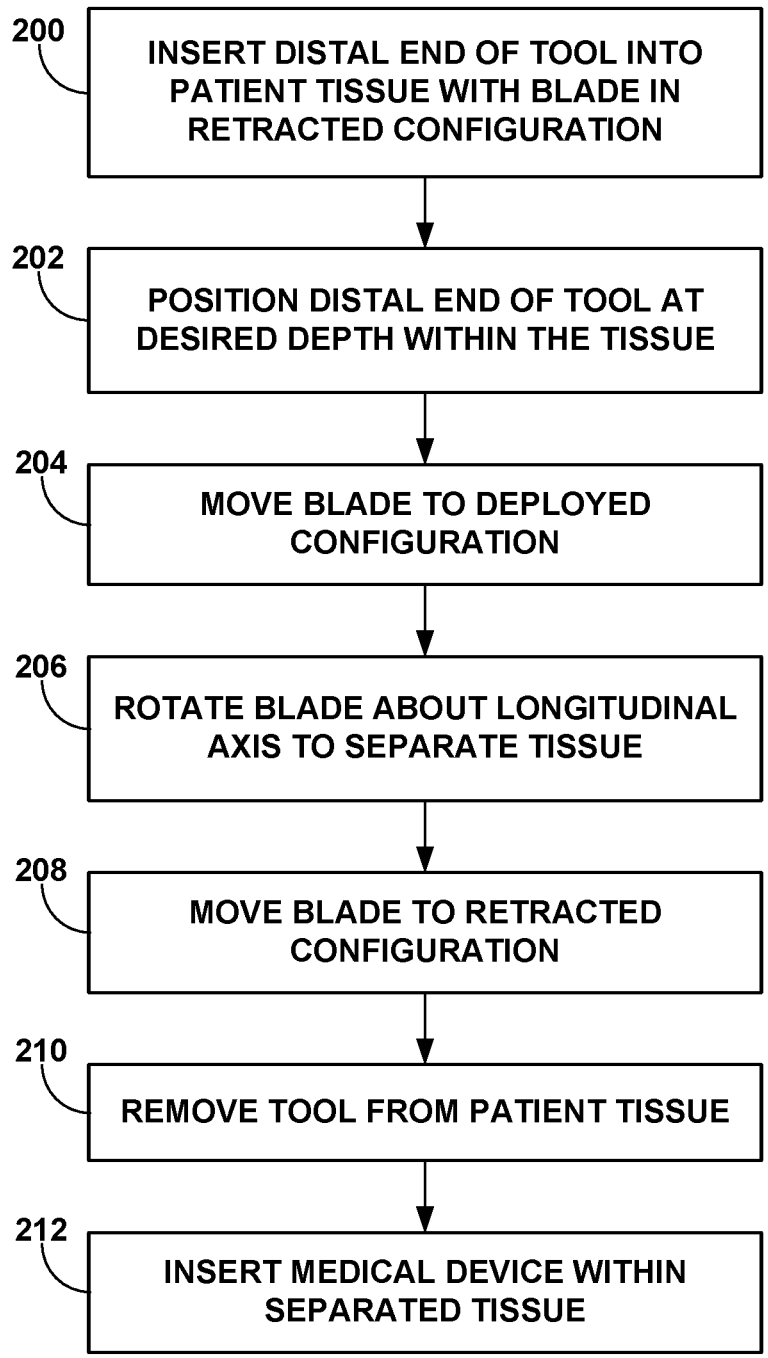
FIG. 13 is a flow diagram of an example technique for creating a tissue pocket using an example surgical tool described herein.

FIG. 13 is a flow diagram of an example technique for creating a tissue pocket using an example surgical tool described herein. In the example of FIG. 13, surgical tool 100 will be described for creating the tissue pocket 160 for IMD 170. However, any surgical tool described herein may be used to create the tissue pocket for any type of IMD.

The clinician may insert the distal end of surgical tool 100 (e.g., blade 112) into patient tissue with blade 112 in the retracted configuration (200). The clinician may then position the distal end of surgical tool 100 at the desired or specified depth within the tissue, such as within adipose tissue 132 (202). For example, the desired depth may correspond to the depth at which blade 112 will be disposed once moved into the deployed configuration. In some examples, surgical tool 100 may include depth stop 106. Therefore, the clinician may stop inserting surgical tool 100 when distal surface 110 of depth stop 106 contacts the exterior surface of the skin of the patient.

Once at the specified depth, the clinician can move blade 112 into the deployed configuration (204). For example, the clinician may actuate a control, such as control 102 on handle 101, to move blade 112 into the deployed configuration. The clinician then rotates blade 112 around longitudinal axis 142 to separate the tissue in the path of blade 112 (206). In some examples, the clinician may rotate blade 112 at least 360 degrees about longitudinal axis 142 to create a complete separation between tissue above and below where IMD 170 will be implanted. Tissue pocket 160 may be disk-shaped from the rotation of blade 112 about longitudinal axis 142.

The separation of tissue creates the tissue pocket, such as tissue pocket 160. Once the tissue pocket is created, the clinician can move blade 112 back to the retracted configuration (208). The clinician can then remote surgical tool 100 from patient tissue (210). The clinician can then insert IMD 170 into tissue pocket 160 that has been formed between the portions of separate tissue (212).

Figure 14A:
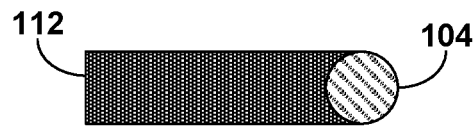
FIGS. 14A, 14B, and 14C are top views of example blades of a surgical tool for separating tissue.
Figure 14B:
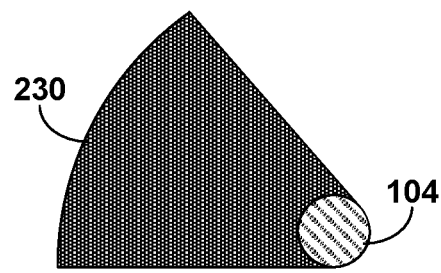
Figure 14C:
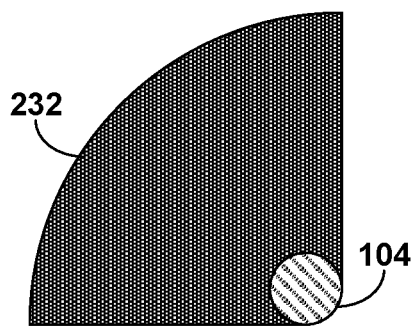

FIGS. 14A, 14B, and 14C are top views of example blades of surgical tool 100 for separating tissue. FIG. 14A shows the top profile of blade 112 attached to shaft 104. Blade 112 may have a rectangular-shaped blade. FIG. 14B shows the top profile of blade 230 attached to shaft 104. Blade 230 has a triangular-shaped profile with a curved distal edge, where the side edges of blade 230 are separated by an approximately 45 degree angle with respect to shaft 104. FIG. 14C shows the top profile of blade 232 attached to shaft 104. Blade 232 has a triangular-shaped profile with a curved distal edge, where the side edges of blade 232 are separated by approximately 90 degrees. Other blades may also be used with different angles separating the side edges. In some examples, a triangular-shaped profile may have a straight distal edge, serrated distal edge, or other shape that may promote tissue cutting and separation.

Figure 15A:
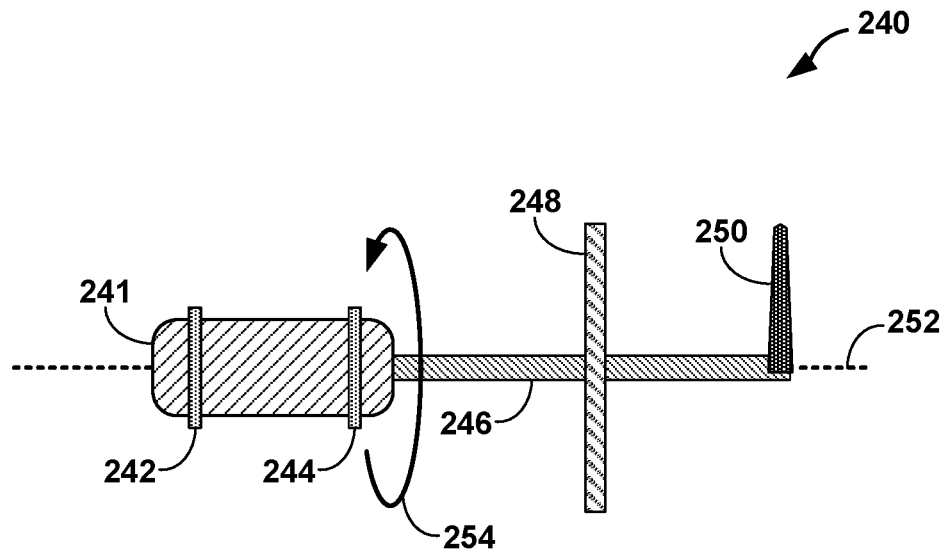
FIGS. 15A and 15B are conceptual diagrams illustrating an example control for circumferentially expanding a plurality of blades of an example surgical tool.
Figure 15B:
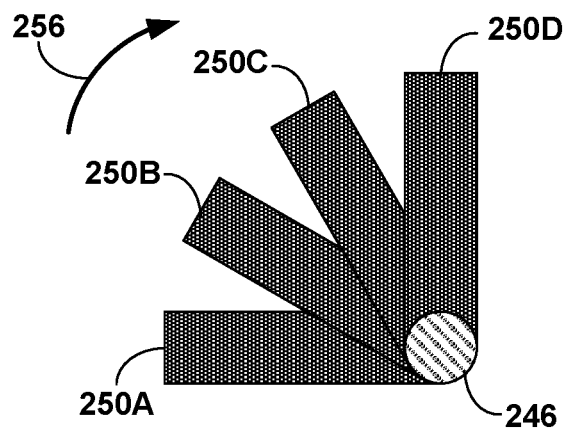

FIGS. 15A and 15B are conceptual diagrams illustrating an example control 244 for circumferentially expanding a plurality of blades 250 of an example surgical tool 240. Surgical tool 240 may be similar to surgical tool 100 described herein. As shown in FIG. 15A, surgical tool 240 includes handle 241, first control 242, second control 244, shaft 246, depth stop 248, and blades 250. Actuation of first control 242 may change blades 250 from the retracted configuration along longitudinal axis 252 to the deployed configuration where blades 250 are extended substantially perpendicular to longitudinal axis 252.

In some examples, a bracket may attach the two or more blades 250 to a hinge that enables blades 250 to move between the retracted configuration and the deployed configuration. First control 242 may be mechanically coupled to the bracket attaching blades 250 to the hinge. Actuation of first control 242 moves the bracket with respect to shaft 246 to pivot the hinge between the retracted configuration and the deployed configuration. Second control 244 may be mechanically coupled to blade 250. For example, second control 244 may rotate about longitudinal axis 252 to extend a rod that pushes each blade of blades 250 into a spread or fanned configuration. In this manner, actuation of second control 244 moves the blades 250 between a stacked configuration and a fanned out configuration.

As shown in FIG. 15B, blade 250A, blade 250B, blade 250C, blade 250D (collectively "blades 250"), have been fanned out in the direction of arrow 256. In the fanned out configuration, the distal ends of each blade of blades 250 have been separated in the circumferential direction. Blades 250 are shown to be fanned out over an approximate 90 degree arc. However, blades 250 may be fanned out over a larger or smaller arc in other examples. For example the arc of the fan may be 45 degrees, 90 degree, 120 degrees, or 180 degrees. In other examples, the fanned out configuration may position each blade equally spaced from the other blades over 360 degrees.

Figure 16:
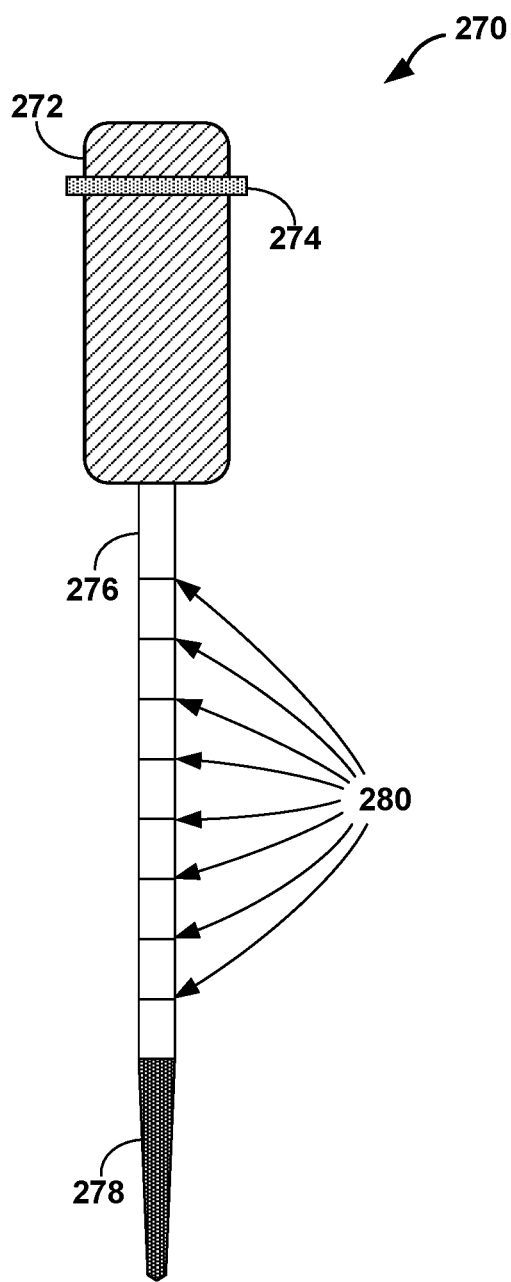
FIG. 16 is a conceptual diagram illustrating an example surgical tool including graduated markings that indicate a depth of the distal end of the tool within tissue.

FIG. 16 is a conceptual diagram illustrating an example surgical tool 270 including graduated markings 280 that indicate a depth of the distal end of the tool within tissue. Surgical tool 270 may be similar to surgical tool 100 and 240. As shown in FIG. 16, surgical tool 270 includes handle 272, control 274, shaft 276, and blade 278. Instead of a depth stop, surgical tool 270 includes graduated markings 280 dispersed along the axial length of shaft 276. Graduated markings 280 may be painted on, molded into, or etched into the outer surface of shaft 276. Graduated markings 280 may indicate the distance in millimeters, centimeters, inches, or an arbitrary scale that the distal end of shaft 276 is into tissue. Graduated markings 280 may indicate the depth at which blade 278 will create the tissue pocket in the deployed configuration. In other examples, graduated markings 280 may indicate the distance to the tip of blade 278 in the retracted configuration. In some examples, a depth stop (e.g., depth stop 106), may be included on shaft 276 in addition to graduated markings 280.

Figure 17A:
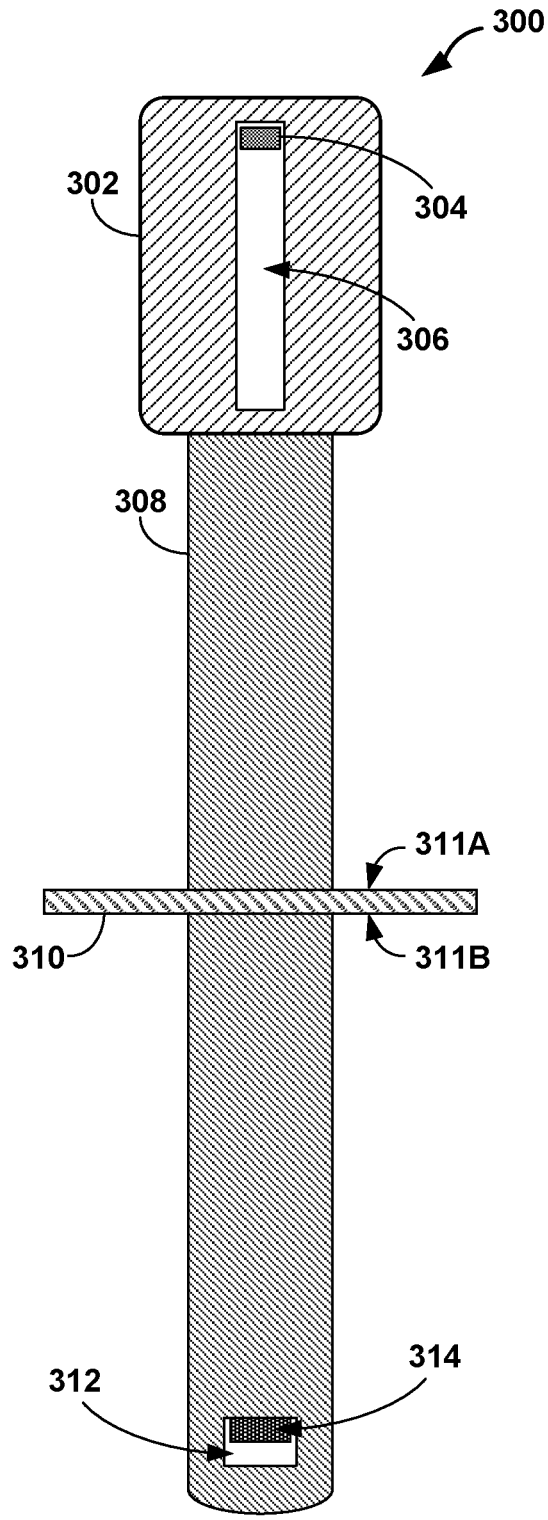
FIGS. 17A and 17B are side and cross-sectional views of an example surgical tool for separating tissue.
Figure 17B:
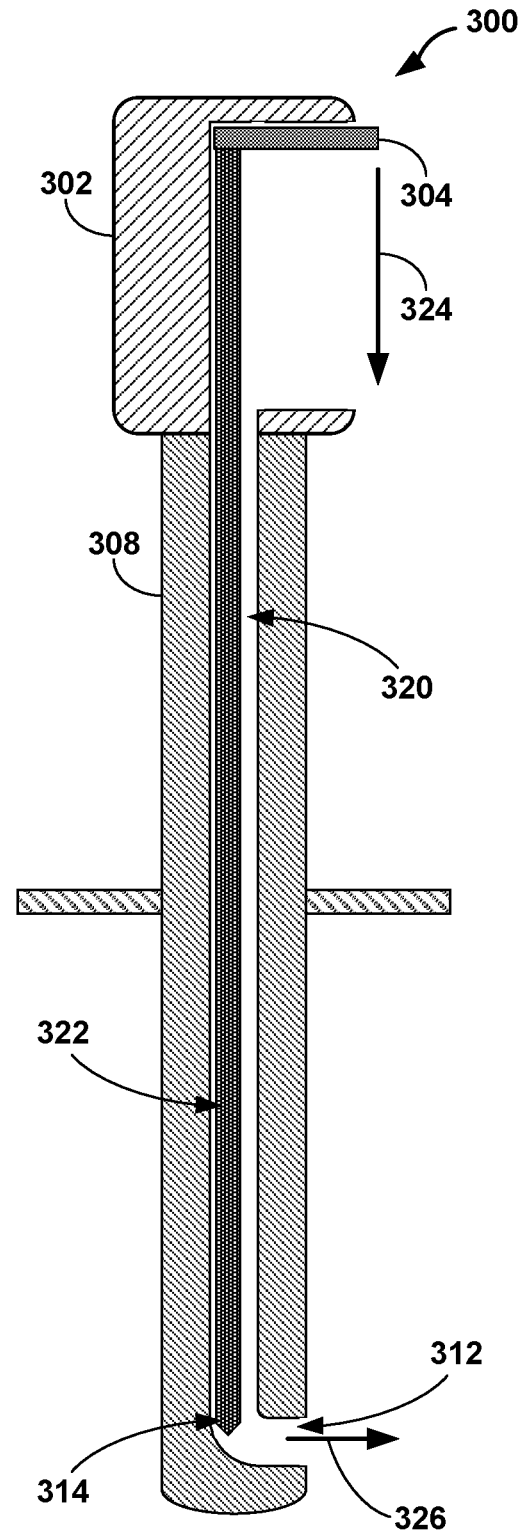

FIGS. 17A and 17B are side and cross-sectional views of an example surgical tool 300 for separating tissue. Surgical tool 300 is similar to surgical tools 100, 240, and 270, but surgical tool 300 extends blade 322 out from within lumen 320 of shaft 308. As shown in FIG. 17A, surgical tool 300 includes a handle 302, slider 304, shaft 308, depth stop 310, and blade tip 314. Handle 302 defines a slot 306, where slider 304 can move within slot 306. Slider 304 may be attached to blade 322 within shaft 308, and movement of slider 304 through slot 306 will cause blade tip 314 to extend from shaft 308. When blade tip 314 remains within shaft 308, blade 322 is in the retracted configuration. Depth stop 310 includes proximal surface 311A and distal surface 311B. Distal surface 311B is configured to contact the external surface of the skin.

FIG. 17B is a cross-sectional view of surgical tool 300. As shown in FIG. 17B, shaft 308 defines a side wall and lumen 320 radially inward from the side wall. The side wall of shaft 308 also defines exit port 312, where exit port 312 is an opening through which blade 322 can exit from lumen 320 of shaft 308. Blade 322 may be a bendable member, such as stainless steel or a flexible polymer. In some example, the bendable member of blade 322 may be constructed of a shape-memory material such as nitinol. Slider 304 may be a control that is configured to move blade 322 axially through lumen 320 and out of exit port 312. A curved wall 314 at the distal end of lumen 320 may force blade tip 314 to bend and exit out of exit port 312 in the direction of arrow 312. For example, once out of exit port 312, blade 322 may remain substantially perpendicular to the outer surface of shaft 308 and the longitudinal axis defined by shaft 308. In this manner, actuation of slider 304 (e.g., a control) may move the bendable member of blade 322 distally along lumen 320 from the retracted configuration within lumen 320 to a deployed configuration in which a distal portion of blade 322 exits radially outward from exit port 312.

Figure 18:
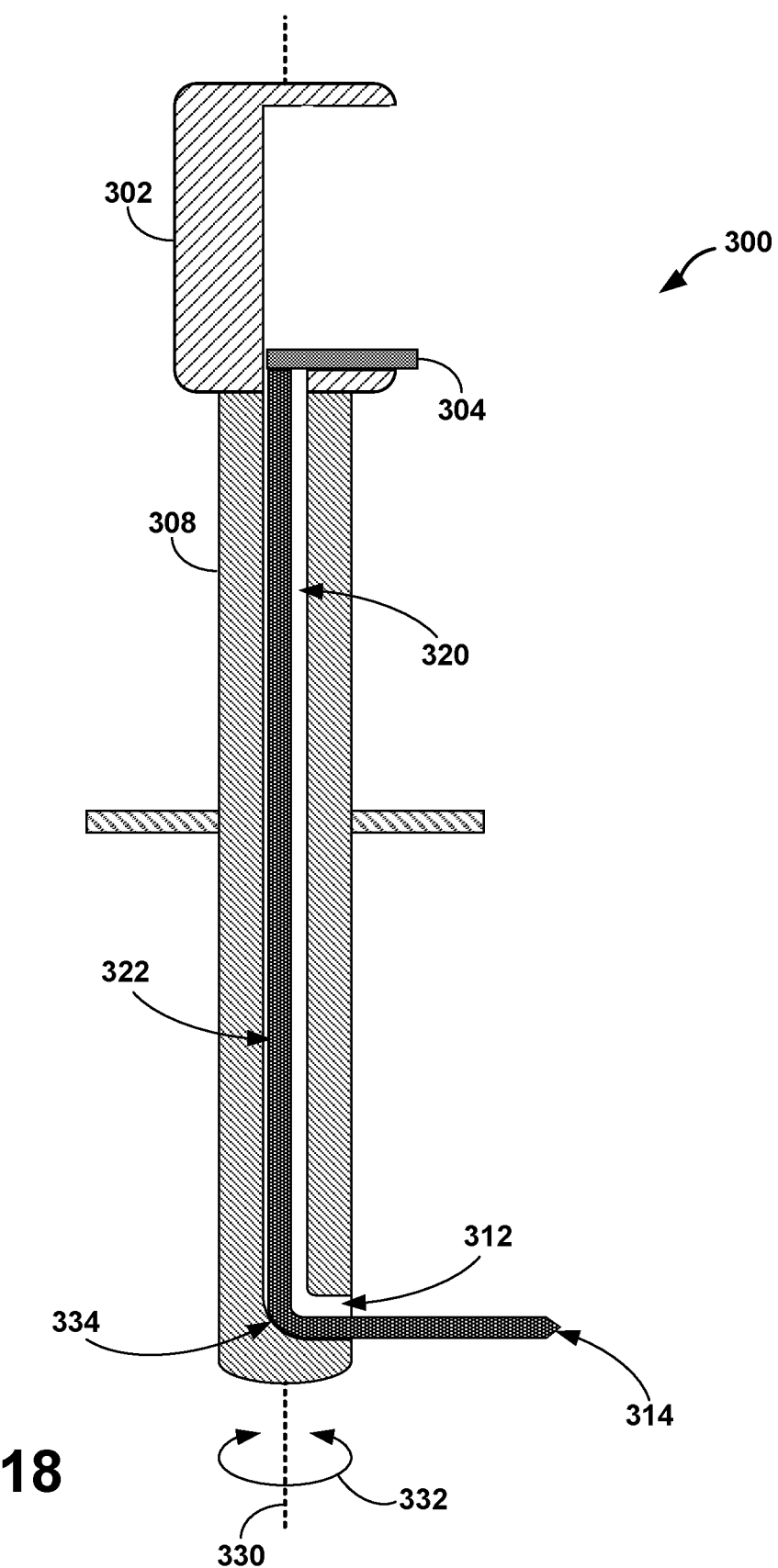
FIG. 18 is a cross-sectional view of the example surgical tool of FIGS. 17A and 17B with a blade in a deployed configuration.

FIG. 18 is a cross-sectional view of the example surgical tool 300 with blade 322 in the deployed configuration. As shown in FIG. 18, the distal end of blade 322 has been deflected by curved wall 334 and out of exit port 312 into the deployed configuration. For example, the clinician has pushed slider 304 to the end of slot 306. Once in the deployed configuration, the clinician may rotate surgical device 300 and blade 314 about longitudinal axis 330 in the direction of arrow 332. Although blade 314 may be rotated in either direction about longitudinal axis 330, blade 314 may be configured to be rotated in only one direction in other examples.

The following examples are described herein. Example 1: a surgical tool comprising a shaft defining a proximal end, a distal end, and a longitudinal axis, a handle coupled to the proximal end of the shaft, and one or more blades configured to move between a retracted configuration and a deployed configuration, wherein the one or more blades extend, in the deployed configuration, substantially perpendicular to the longitudinal axis at the distal end of the shaft, and wherein the one or more blades are configured to separate tissue in the deployed configuration.

Example 2: the surgical tool of example 1, wherein the one or more blades are attached to the distal end of the shaft via a hinge, and wherein the hinge is configured to move the blades between the retracted configuration and the deployed configuration.

Example 3: the surgical tool of example 2, further comprising a control mechanically coupled to the one or more blades, wherein actuation of the control pivots the hinge between the retracted configuration and the deployed configuration.

Example 4: the surgical tool of any of examples 1 through 3, wherein the one or more blades comprise at least one beveled edge configured to cut tissue.

Example 5: the surgical tool of any of examples 1 through 4, wherein each blade of the one or more blades comprises a length between approximately 1.0 cm and 8.0 cm, and wherein the length is greater than a width of each blade of the one or more blades.

Example 6: the surgical tool of any of examples 1 through 5, wherein each blade of the one or more blades defines a width and a thickness, wherein the width is greater than the thickness.

Example 7: the surgical tool of any of examples 1 through 6, wherein each blade of the one or more blades comprises a proximal end and a distal end, wherein the distal end has a first dimension wider than a second dimension of the proximal end.

Example 8: the surgical tool of any of examples 1 through 7, wherein the one or more blades comprise at least two blades.

Example 9: the surgical tool of example 8, further comprising a first control mechanically coupled to a bracket attaching the at least two blades to the hinge, wherein actuation of the first control moves the bracket with respect to the shaft to pivot the hinge between the retracted configuration and the deployed configuration, and a second control mechanically coupled to the at least two blades, wherein actuation of the second control moves the at least two blades between a stacked configuration and a fanned out configuration.

Example 10: the surgical tool of any of examples 1 through 9, wherein the shaft defines side wall and a lumen radially inward from the side wall, wherein the side wall defines an exit port, wherein the one or blades comprise a bendable member, and wherein the surgical tool further comprises a control configured to move the bendable member distally along the lumen from the retracted configuration within the lumen to a deployed configuration in which a distal portion of the bendable member exits radially outward from the exit port.

Example 11: the surgical tool of any of examples 1 through 10, wherein the shaft comprises a plurality of graduated markings configured to indicate a depth of the distal end of the shaft within tissue.

Example 12: the surgical tool of any of examples 1 through 11, further comprising a depth stop disposed at an axial position along the shaft, wherein the depth stop is configured to contact skin and prevent the shaft and the one or more blades from being inserted further into tissue.

Example 13: the surgical tool of example 12, wherein the depth stop comprises disk having a first radius at least half of a second radius of the one or more blades in the deployed configuration.

Example 14: the surgical tool of any of examples 12 and 13, wherein the axial position is a first axial position, and wherein the depth stop is configured to move from the first axial position to a second axial position along the shaft.

Example 15: a method comprising: inserting a distal portion of shaft of a surgical tool into tissue of a patient, the shaft defining a distal end, a proximal end, and a longitudinal axis; moving one or more blades from a retracted configuration to a deployed configuration, wherein the one or more blades extend, in the deployed configuration, substantially perpendicular to the longitudinal axis at the distal end of the shaft; and rotating the one or more blades in the deployed position to separate a first portion of tissue from a second portion of tissue such that an implantable medical device is insertable between the first portion of tissue and the second portion of tissue.

Example 16: the method of example 15, wherein moving the one or more blades from the retracted configuration to the deployed configuration comprises actuating a control that is mechanically coupled to the one or more blades to pivot a hinge configured to move the blades between the retracted configuration to the deployed configuration.

Example 17: the method of example 16, wherein the control is a first control and the one or more blades comprises at least two blades, and wherein the method further comprises actuating a second control to move the at least two blades between a stacked configuration and a fanned out configuration.

Example 18: the method of any of examples 15 through 17, wherein rotating the one or more blades in the deployed position comprises rotating a leading edge of the one or more blades at least 360 degrees around the longitudinal axis to create a disk-shaped pocket between the first portion of tissue and the second portion of tissue.

Example 19: the method of any of examples 15 through 17, wherein inserting the distal portion of shaft comprises inserting the distal portion of the shaft until a depth stop disposed at an axial position along the shaft contacts an external surface of skin of the patient.

Example 20: a surgical tool comprising: a shaft defining a proximal end, a distal end, and a longitudinal axis; a handle coupled to the proximal end of the shaft; one or more blades configured to move between a retracted configuration and a deployed configuration, wherein: the one or more blades extend, in the deployed configuration, substantially perpendicular to the longitudinal axis at the distal end of the shaft, the one or more blades are attached to the distal end of the shaft via a hinge, and wherein the hinge is configured move the blades between the retracted configuration and the deployed configuration, and each blade of the one or more blades comprises a length between approximately 1.0 cm and 8.0 cm, the length being greater than a width of the one or more blades; a depth stop disposed at an axial position along the shaft, wherein the depth stop is configured to contact skin and prevent the shaft and the one or more blades from being inserted further into tissue; and a control mechanically coupled to the one or more blades, wherein actuation of the control pivots the hinge between the retracted configuration and the deployed configuration.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. For example, any module described herein may include electrical circuitry configured to perform the features attributed to that particular module, such as fixed function processing circuitry, programmable processing circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A surgical tool comprising:
a shaft defining a proximal end, a distal end, and a longitudinal axis;
a handle coupled to the proximal end of the shaft; and
two or more blades configured to move between a retracted configuration and a deployed configuration, wherein the two or more blades extend, in the deployed configuration, substantially perpendicular to the longitudinal axis at the distal end of the shaft, wherein the two or more blades are configured to separate tissue in the deployed configuration, and wherein:
a length of each blade of the two or more blades is parallel with a direction that respective blade extends from the shaft,
a width of each blade of the two or more blades is greater than and orthogonal to a thickness of each blade of the two or more blades, and
the thickness of each blade is parallel with the longitudinal axis of the shaft when the blade is in the deployed configuration,
wherein each blade of the two or more blades is configured to extend from the longitudinal axis in a different respective circumferential direction from other blades of the two or more blades such that an end of each blade is separated from other blades of the two or more blades by a respective gap.

2. The surgical tool of claim 1, wherein the two or more blades are attached to the distal end of the shaft via a hinge, and wherein the hinge is configured to move the two or more blades between the retracted configuration and the deployed configuration.

3. The surgical tool of claim 2, further comprising a control mechanically coupled to the two or more blades, wherein actuation of the control pivots the hinge between the retracted configuration and the deployed configuration.

4. The surgical tool of claim 1, wherein each blade of the two or more blades comprises at least one beveled edge along at least a portion of the length of each blade, the at least one beveled edge configured to cut through the tissue as the two or more blades are rotated about the longitudinal axis.

5. The surgical tool of claim 1, wherein the length is between approximately 1.0 cm and 8.0 cm, and wherein the length is greater than the width of each blade of the two or more blades.

6. The surgical tool of claim 1, wherein each blade of the two or more blades comprises a proximal end and a distal end, wherein the distal end of the two or more blades has a first dimension wider than a second dimension of the proximal end of the two or more blades.

7. The surgical tool of claim 1, further comprising:
a first control mechanically coupled to a bracket attaching the two or more blades to a hinge, wherein actuation of the first control moves the bracket with respect to the shaft to pivot the hinge between the retracted configuration and the deployed configuration; and
a second control mechanically coupled to the two or more blades, wherein actuation of the second control moves the two or more blades between a stacked configuration and a fanned out configuration.

8. The surgical tool of claim 1, wherein the shaft defines side wall and a lumen radially inward from the a side wall, wherein the side wall defines an exit port, wherein the two or more blades comprise a bendable member, and wherein the surgical tool further comprises a control configured to move the bendable member distally along the lumen from the retracted configuration within the lumen to a deployed configuration in which a distal portion of the bendable member exits radially outward from the exit port.

9. The surgical tool of claim 1, wherein the shaft comprises a plurality of graduated markings configured to indicate a depth of the distal end of the shaft within tissue.

10. The surgical tool of claim 1, further comprising a depth stop disposed at an axial position along the shaft, wherein the depth stop is configured to contact skin and prevent the shaft and the two or more blades from being inserted further into tissue.

11. The surgical tool of claim 10, wherein the depth stop comprises a disk having a first radius at least half of a second radius of the two or more blades in the deployed configuration.

12. The surgical tool of claim 10, wherein the axial position is a first axial position, and wherein the depth stop is configured to move from the first axial position to a second axial position along the shaft.

13. A method comprising:
inserting a distal portion of a shaft of a surgical tool into tissue of a patient, the shaft defining a distal end, a proximal end, and a longitudinal axis;
moving two or more blades from a retracted configuration to a deployed configuration, wherein the two or more blades extend, in the deployed configuration, substantially perpendicular to the longitudinal axis at the distal end of the shaft; and
rotating the two or more blades in the deployed position to separate a first portion of tissue from a second portion of tissue such that an implantable medical device is insertable between the first portion of tissue and the second portion of tissue, wherein a length of each blade of the two or more blades is parallel with a direction that respective blade extends from the shaft, wherein a width of each blade of the two or more blades is greater than and orthogonal to a thickness of each blade of the two or more blades, and wherein the thickness of each blade is parallel with the longitudinal axis of the shaft when the blade is in the deployed configuration,
wherein each blade of the two or more blades is configured to extend from the longitudinal axis in a different respective circumferential direction from other blades of the two or more blades such that an end of each blade is separated from other blades of the two or more blades by a respective gap.

14. The method of claim 13, wherein moving the two or more blades from the retracted configuration to the deployed configuration comprises actuating a control that is mechanically coupled to the two or more blades to pivot a hinge configured to move the two or more blades between the retracted configuration to the deployed configuration.

15. The method of claim 14, wherein the method further comprises actuating a second control to move the two or more blades between a stacked configuration and a fanned out configuration.

16. The method of claim 13, wherein rotating the two or more blades in the deployed position comprises rotating a leading edge of the two or more blades at least 360 degrees around the longitudinal axis to create a disk-shaped pocket between the first portion of tissue and the second portion of tissue.

17. The method of claim 13, wherein inserting the distal portion of shaft comprises inserting the distal portion of the shaft until a depth stop disposed at an axial position along the shaft contacts an external surface of skin of the patient.

18. A surgical tool comprising:
a shaft defining a proximal end, a distal end, and a longitudinal axis;
a handle coupled to the proximal end of the shaft;
two or more blades configured to move between a retracted configuration and a deployed configuration, wherein:
the two or more blades extend, in the deployed configuration, substantially perpendicular to the longitudinal axis at the distal end of the shaft,
the two or more blades are attached to the distal end of the shaft via a hinge, and wherein the hinge is configured move the two or more blades between the retracted configuration and the deployed configuration,
each blade of the two or more blades comprises a length parallel with a direction that respective blade extends from the shaft, the length between approximately 1.0 cm and 8.0 cm, and the length being greater than a width of the two or more blades,
the width of each blade of the two or more blades is greater than and orthogonal to a thickness of each blade of the two or more blades, and
the thickness of each blade is parallel with the longitudinal axis of the shaft when the blade is in the deployed configuration;
a depth stop disposed at an axial position along the shaft, wherein the depth stop is configured to contact skin and prevent the shaft and the two or more blades from being inserted further into tissue; and
a control mechanically coupled to the two or more blades, wherein actuation of the control pivots the hinge between the retracted configuration and the deployed configuration,
wherein each blade of the two or more blades is configured to extend from the longitudinal axis in a different respective circumferential direction from other blades of the two or more blades such that an end of each blade is separated from other blades of the two or more blades by a respective gap.

* * * * *